(12) United States Patent
Park et al.

(10) Patent No.: US 8,616,214 B2
(45) Date of Patent: Dec. 31, 2013

(54) EARPLUG HAVING A RESILIENT CORE STRUCTURE

(75) Inventors: KangSoo Park, Gyeonggi-do (KR); JungMo Kim, Gyeonggi-do (KR); InYoung Sa, Gyeonggi-do (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 125 days.

(21) Appl. No.: 13/080,980

(22) Filed: Apr. 6, 2011

(65) Prior Publication Data

US 2012/0255564 A1 Oct. 11, 2012

(51) Int. Cl.
*A61F 11/00* (2006.01)

(52) U.S. Cl.
USPC .......................................... 128/864; 128/865

(58) Field of Classification Search
USPC .................. 128/864–865; 181/129–130, 135; 623/1.15, 1.32, 10
See application file for complete search history.

(56) References Cited

U.S. PATENT DOCUMENTS

| | | | |
|---|---|---|---|
| 4,334,315 A | 6/1982 | Ono et al. | |
| 4,375,016 A | 2/1983 | Harada | |
| 4,442,917 A | 4/1984 | Johnson | |
| 4,498,332 A | 2/1985 | Bruckhoff | |
| 4,539,440 A * | 9/1985 | Sciarra | 381/329 |
| 4,556,122 A | 12/1985 | Goode | |
| 4,582,053 A * | 4/1986 | Wilson | 128/867 |
| 4,724,922 A | 2/1988 | Kalayjian | |
| 4,834,927 A | 5/1989 | Birkholz et al. | |
| 4,878,560 A | 11/1989 | Scott | |
| 4,913,259 A | 4/1990 | Packard | |
| 5,002,151 A | 3/1991 | Oliveira et al. | |
| 5,046,580 A | 9/1991 | Barton | |
| 5,131,411 A | 7/1992 | Casali et al. | |
| 5,146,619 A | 9/1992 | Brown | |
| 5,201,007 A | 4/1993 | Ward et al. | |
| 5,440,082 A | 8/1995 | Claes | |
| 5,487,012 A | 1/1996 | Topholm et al. | |
| 6,006,857 A | 12/1999 | Leight et al. | |
| 6,205,227 B1 | 3/2001 | Mahoney et al. | |
| 6,241,041 B1 | 6/2001 | Leight | |

(Continued)

FOREIGN PATENT DOCUMENTS

| | | |
|---|---|---|
| CN | 201079491 Y | 7/2008 |
| DE | 2318735 A1 | 10/1974 |

(Continued)

OTHER PUBLICATIONS

International Search Report and Written Opinion for PCT/IB2012/051031 dated Sep. 25, 2012.

*Primary Examiner* — Patricia Bianco
*Assistant Examiner* — Camtu Nguyen
(74) *Attorney, Agent, or Firm* — Armstrong Teasdale LLP

(57) ABSTRACT

An earplug for insertion into an ear canal of a user has a front, a back, a side extending between the front and the back, a longitudinal axis, and a transverse axis. A core structure is selectively moveable from an un-deformed position to a deformed, insertable position suitable for insertion of the earplug into the ear canal of the user. A cover covers at least a portion of the core structure and is adapted for contact with the ear canal of the user. An actuator is operatively connected to the core structure for moving the core structure from the un-deformed position to the deformed, insertable position upon application of a force to the actuator.

20 Claims, 28 Drawing Sheets

(56) References Cited

U.S. PATENT DOCUMENTS

| | | |
|---|---|---|
| 6,256,396 B1 | 7/2001 | Cushman |
| 6,397,087 B1 | 5/2002 | Kim et al. |
| 6,401,859 B1 | 6/2002 | Widmer et al. |
| 6,533,062 B1 | 3/2003 | Widmer et al. |
| 6,549,635 B1 | 4/2003 | Gebert |
| 6,567,524 B1 | 5/2003 | Svean et al. |
| 6,595,317 B1 | 7/2003 | Widmer et al. |
| 6,661,901 B1 | 12/2003 | Svean et al. |
| 6,754,359 B1 | 6/2004 | Svean et al. |
| 7,130,437 B2 | 10/2006 | Stonikas et al. |
| 7,362,875 B2 | 4/2008 | Saxton et al. |
| 7,387,187 B2 | 6/2008 | Widmer et al. |
| 7,537,011 B2 | 5/2009 | Falco |
| 7,571,018 B2 | 8/2009 | Roth et al. |
| 7,602,933 B2 | 10/2009 | Cartwright et al. |
| 7,605,812 B2 | 10/2009 | McBagonluri et al. |
| 7,627,131 B2 | 12/2009 | Nielsen et al. |
| 7,720,244 B2 | 5/2010 | Espersen et al. |
| 7,778,434 B2 | 8/2010 | Juneau et al. |
| 7,779,844 B2 | 8/2010 | Purcell et al. |
| 2004/0045558 A1 | 3/2004 | Taylor et al. |
| 2006/0042868 A1 | 3/2006 | Berg et al. |
| 2006/0050912 A1 | 3/2006 | Kidd et al. |
| 2006/0067556 A1 | 3/2006 | Bailey et al. |
| 2006/0109995 A1 | 5/2006 | Fischer et al. |
| 2006/0147079 A1 | 7/2006 | Jaakkola |
| 2007/0053522 A1 | 3/2007 | Murray et al. |
| 2007/0057941 A1 | 3/2007 | Fang et al. |
| 2007/0127754 A1 | 6/2007 | Slabaugh et al. |
| 2007/0127756 A1 | 6/2007 | Slabaugh et al. |
| 2007/0221232 A1 | 9/2007 | Jenkins |
| 2008/0037812 A1 | 2/2008 | Fickweiler et al. |
| 2008/0116003 A1 | 5/2008 | Suyama |
| 2008/0152178 A1 | 6/2008 | Topholm et al. |
| 2008/0166001 A1 | 7/2008 | Hankey et al. |
| 2008/0175424 A1 | 7/2008 | McBagonluri et al. |
| 2008/0298618 A1 | 12/2008 | Baumann et al. |
| 2008/0310728 A1 | 12/2008 | Melkisetoglu et al. |
| 2008/0314393 A1 | 12/2008 | Purcell et al. |
| 2009/0038625 A1 | 2/2009 | Cortez et al. |
| 2009/0116677 A1 | 5/2009 | Jones et al. |
| 2009/0136056 A1 | 5/2009 | Franzen |
| 2009/0154749 A1 | 6/2009 | Jorgensen et al. |
| 2009/0202085 A1 | 8/2009 | Gaches |
| 2009/0214072 A1 | 8/2009 | Staab et al. |
| 2009/0245530 A1 | 10/2009 | Keady |
| 2010/0027825 A1 | 2/2010 | Fickweiler et al. |
| 2010/0043806 A1 | 2/2010 | Gehling et al. |
| 2010/0103170 A1 | 4/2010 | Baloch et al. |
| 2010/0177919 A1 | 7/2010 | Giese et al. |
| 2010/0275931 A1 | 11/2010 | Seyed |

FOREIGN PATENT DOCUMENTS

| | | |
|---|---|---|
| EP | 325107 A1 | 7/1989 |
| EP | 0289750 B1 | 7/1991 |
| EP | 958711 A1 | 11/1999 |
| EP | 1151633 A1 | 7/2001 |
| EP | 1320280 A3 | 8/2003 |
| EP | 1276443 B1 | 3/2006 |
| EP | 1345470 B1 | 11/2006 |
| EP | 1776968 A2 | 4/2007 |
| EP | 1322268 B1 | 1/2009 |
| EP | 1313417 B1 | 2/2009 |
| EP | 2027751 A2 | 2/2009 |
| EP | 2027752 A2 | 2/2009 |
| EP | 1313418 B1 | 3/2009 |
| EP | 1853088 B1 | 4/2009 |
| GR | 1005033 B1 | 10/2005 |
| JP | 3145066 U | 9/2008 |
| WO | 9727721 A1 | 7/1997 |
| WO | 9851125 A1 | 11/1998 |
| WO | 0042816 A1 | 7/2000 |
| WO | 0143500 A1 | 6/2001 |
| WO | 0187001 A2 | 11/2001 |
| WO | 0217835 A1 | 3/2002 |
| WO | 0225995 A1 | 3/2002 |
| WO | 2006117408 A2 | 11/2006 |
| WO | 2006117409 A2 | 11/2006 |
| WO | 2007014950 A2 | 2/2007 |
| WO | 2008119088 A1 | 10/2008 |
| WO | 2008139931 A1 | 11/2008 |
| WO | 2009087241 A3 | 7/2009 |
| WO | 2010037752 A1 | 4/2010 |
| WO | 2010040350 A8 | 4/2010 |
| WO | 2010066299 A1 | 6/2010 |

* cited by examiner

EARPLUG HAVING A RESILIENT CORE STRUCTURE

FIELD

The field of this invention relates generally to an earplug for insertion into an ear canal of a user, and more specifically, to an earplug that has a resilient core structure and is capable of engaging the user's ear canal.

BACKGROUND

It is known that hearing protection devices (e.g., earplugs, earmuffs) should be used by individuals exposed to high noise levels. It is also known that hearing protection devices can be used to inhibit water, foreign bodies, dust, or excessive wind from entering the wearer's ear.

Currently available hearing protection devices are often uncomfortable, difficult to use, and/or perform poorly. For example, existing disposable foam earplugs, which are one known type of hearing protection device, require the user to manually compress a portion of the earplug and insert the compressed portion into their ear canal. Once inserted into the ear canal of the user, the compressed earplug is allowed to re-expand and thereby engage the user's ear canal. Foam earplugs can cause discomfort for users with relatively small ear canals in that the more compressed the earplug remains during wear, the greater the force it exerts on the user's ear canal.

Further, existing disposable foam earplugs require the user to roll the foam between their fingers to compress it for proper insertion. If this step is not done, or is insufficiently done, the earplug is often inserted improperly so as to not provide optimal protection. Also, if the user's hands are dirty when compressing the earplug, dirt and/or germs can be transferred to the earplug and then inserted into the ear canal along with the earplug. Moreover, the earplug often rubs against the user's ear during insertion and removal which can chafe or otherwise irritate the user's skin.

In addition, once the earplug is inserted into the ear canal, it often takes tens of seconds to re-expand and engage the user's ear canal. This delay puts the user at risk of exposure if the earplug is inserted under the circumstances from which the user is seeking protection (e.g., a noisy environment, a windy environment).

Moreover, existing disposable foam earplugs seal against the wall of the ear canal during use and at the moment of removal. This potentially causes a vacuum to form within the ear canal as the earplug is being removed, which can make removal difficult and/or uncomfortable.

Accordingly, there remains a need for an earplug that is easy to use (e.g., easy to insert, easy to remove) and relatively quick to sealingly engage with the ear canal of the user when inserted. There is also a need for an earplug that facilitates insertion and removal of the earplug in a hygienic matter.

SUMMARY

In one aspect, an earplug for insertion into an ear canal of a user generally comprises a front, a back, a side extending between the front and the back, a longitudinal axis, and a transverse axis. A core structure is selectively moveable from an un-deformed position to a deformed, insertable position suitable for insertion of the earplug into the ear canal of the user. A cover covers at least a portion of the core structure and is adapted for contact with the ear canal of the user. An actuator extends outward from the back and operatively connected to the core structure for moving the core structure from the un-deformed position to the deformed, insertable position upon application of a force to the actuator generally along the longitudinal axis.

In another aspect, an earplug for insertion into an ear canal of a user generally comprises a front, a back, a side extending between the front and the back, a longitudinal axis, and a transverse axis. A core structure is selectively moveable from an un-deformed position to a deformed, insertable position suitable for insertion of the earplug into the ear canal of the user. The core structure is resilient such that the core structure is biased toward the un-deformed position when in the deformed, insertable position. A cover covers at least a portion of the core structure and is adapted for contact with the ear canal of the user. An actuator is operatively connected to the core structure for moving the core structure from the un-deformed position to the deformed, insertable position.

In yet another aspect, a method of inserting an earplug into an ear canal of an ear generally comprises applying a force to an actuator of the earplug to move a core structure of the earplug from an un-deformed position to a deformed, insertable position wherein the core structure collapses to reduce a width of the earplug. The core structure is resiliently biased from the deformed, insertable portion toward the un-deformed position. The earplug is inserted into the ear canal while the earplug is in the deformed, insertable position. The actuator is released thereby allowing the bias of the core structure to move the core structure from the deformed, insertable position to a partially deformed, inserted position wherein the earplug engages the user's ear canal.

BRIEF DESCRIPTION OF THE DRAWINGS

Corresponding reference characters indicate corresponding parts throughout the several views of the drawings.

DETAILED DESCRIPTION OF THE DRAWINGS

Figure 1:
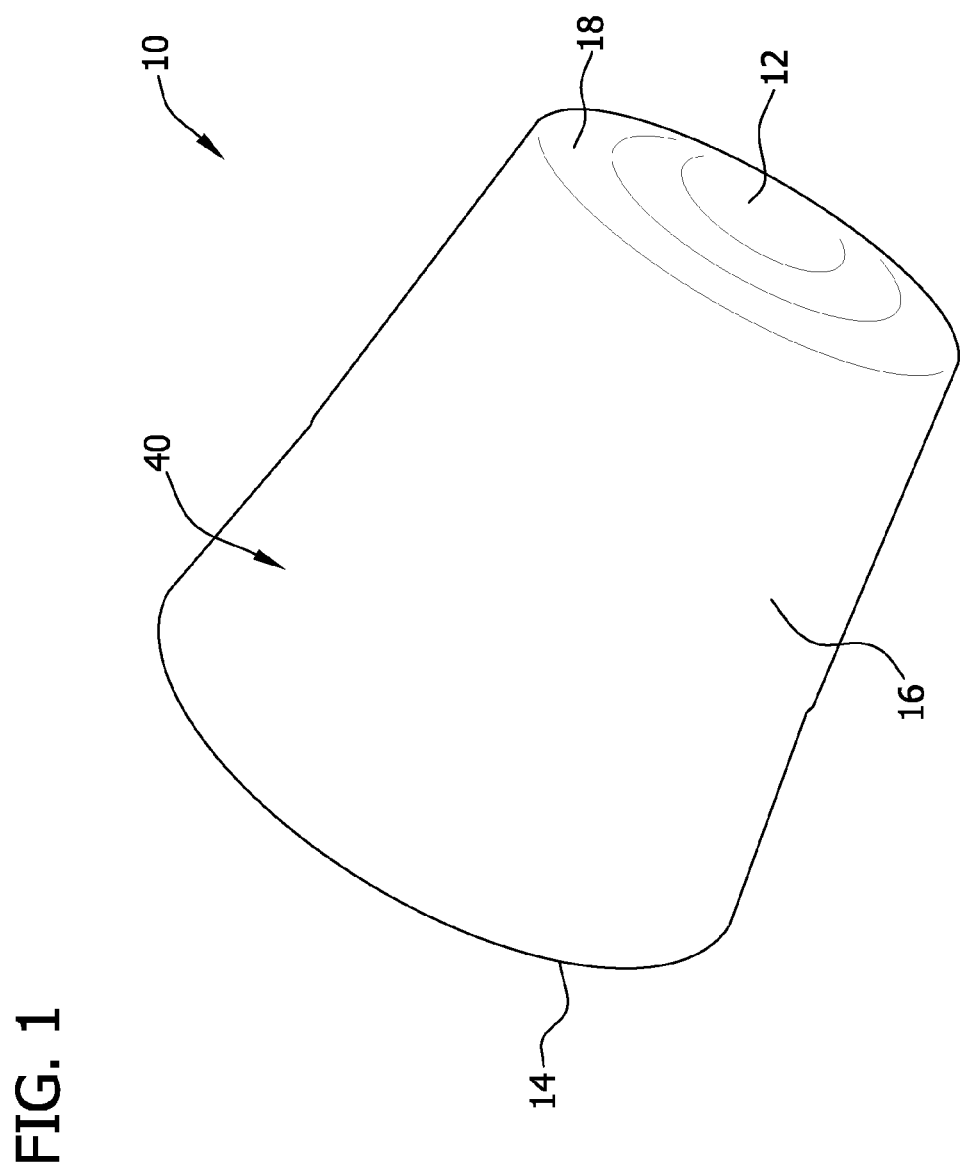
FIG. 1 is a perspective of one suitable embodiment of an earplug.
Figure 2:
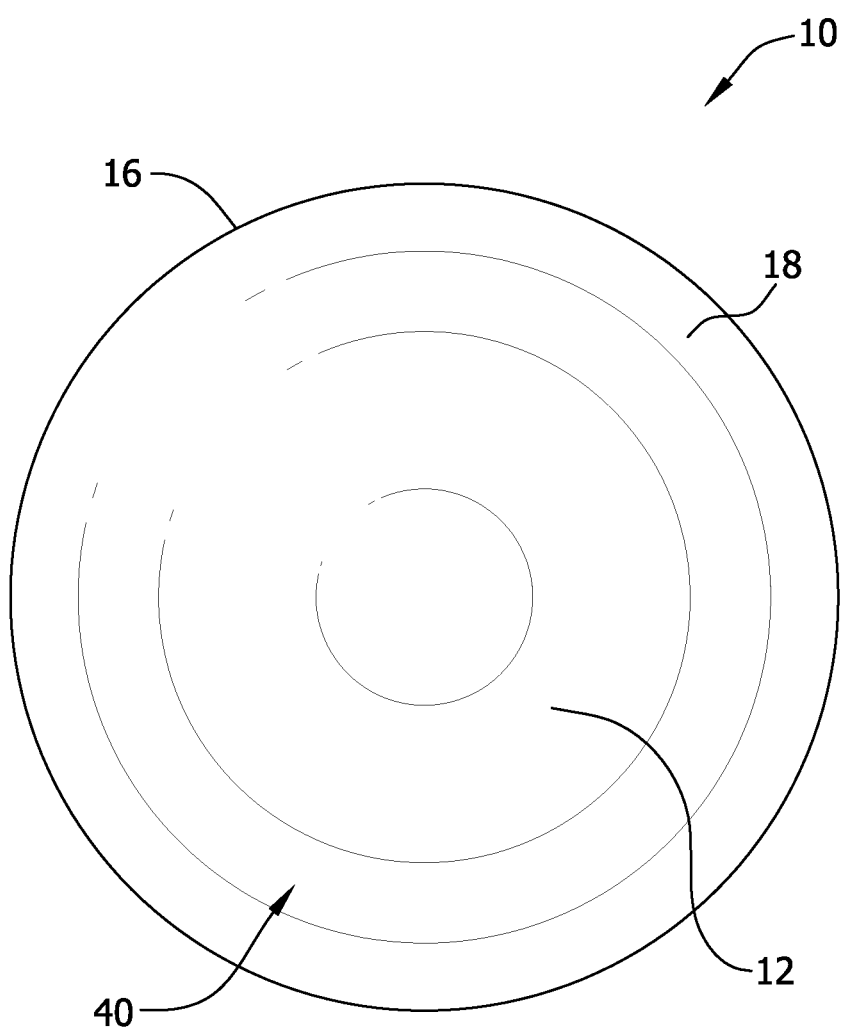
FIG. 2 is a front end view of the earplug of FIG. 1.

Referring now to the drawings, FIGS. 1-5 show one suitable embodiment of an earplug, indicated generally at 10, for insertion into an ear canal of a user. As explained in more detail below, the illustrated earplug 10 is configured to sealingly engage the user's ear canal and provide protection to the user against exposure to high noise levels. It is understood, however, that the earplug 10 can be adapted for use in inhibiting water, foreign bodies, dust, and/or excessive wind from entering the user's ear canal.

Figure 3:
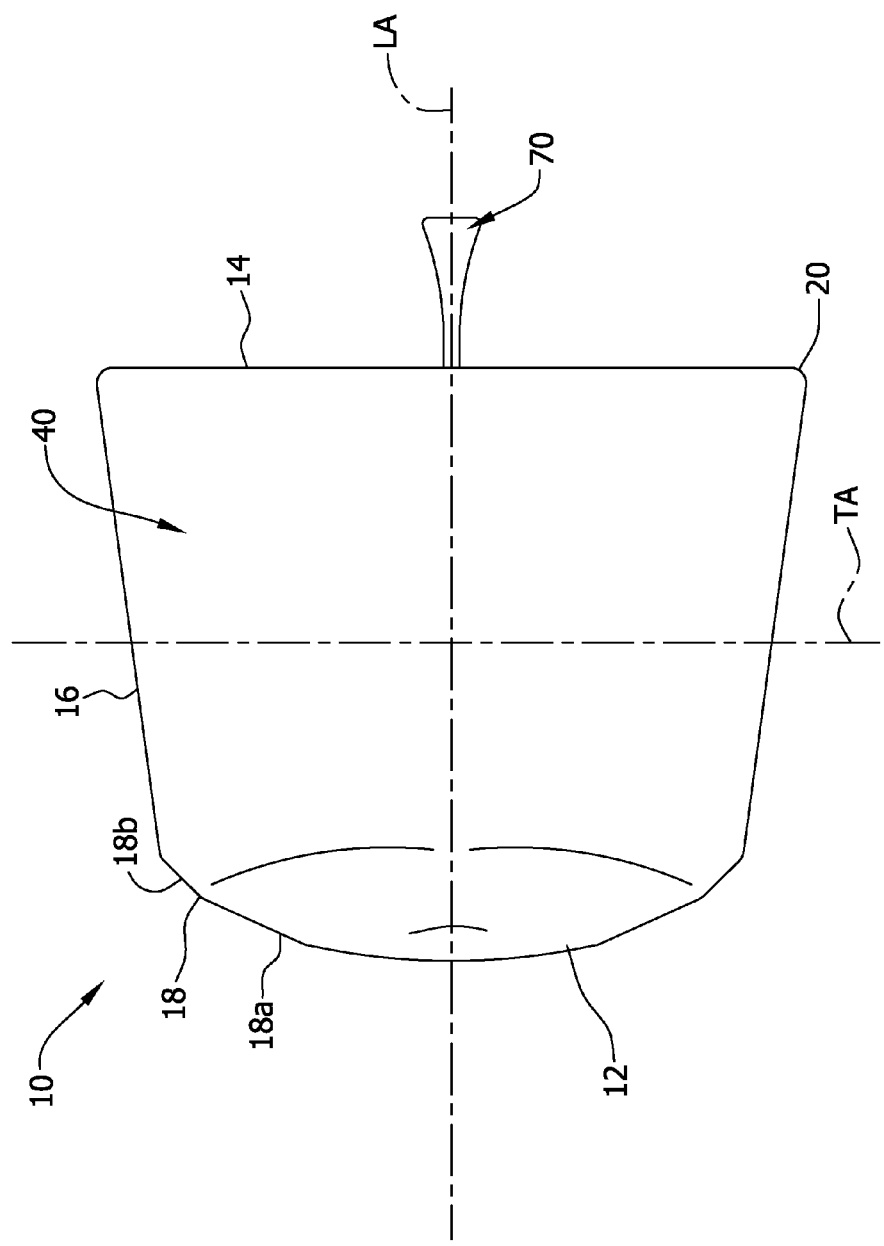
FIG. 3 is a right side view of the earplug.
Figure 4:
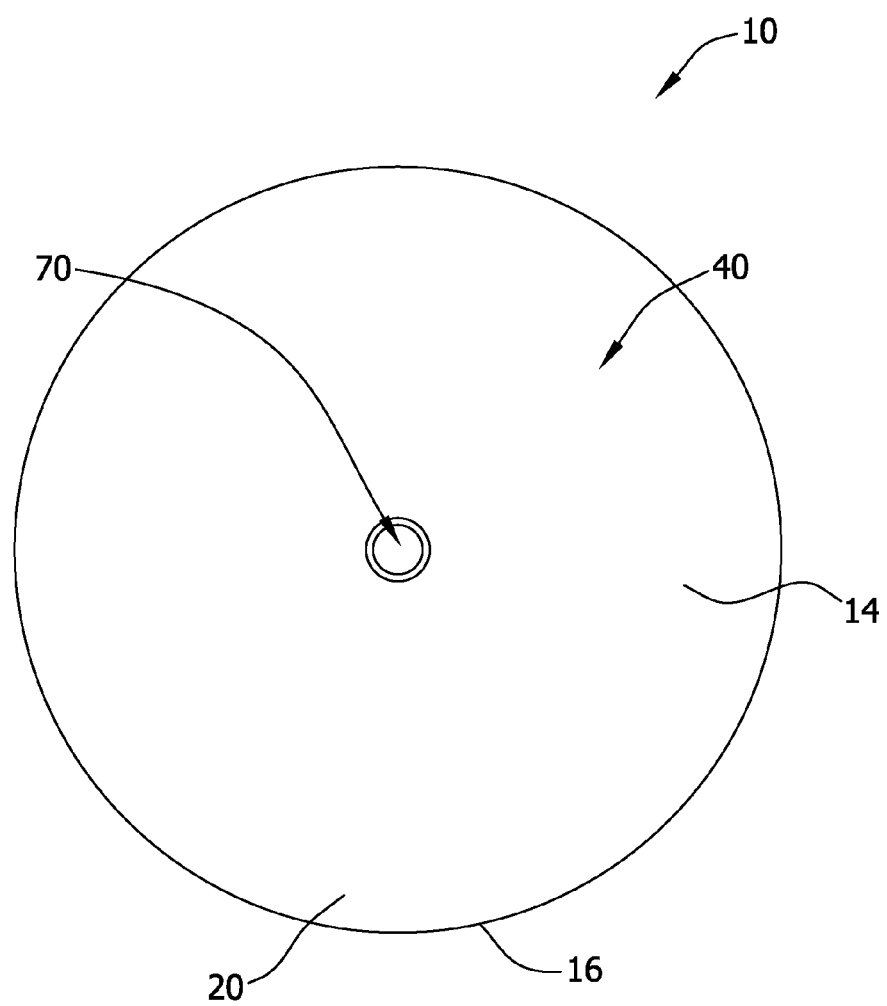
FIG. 4 is a back end view of the earplug.

The earplug 10 has a front 12, a back 14, and a side 16 extending between the front and back. The earplug 10 also has a longitudinal axis LA and a transverse axis TA (FIG. 3). In the illustrated embodiment, the front 12 and the back 14 of the earplug 10 are generally planar (i.e., flat). It is understood, however, that the front 12 and/or the back 14 of the earplug 10 can have different configurations besides planar (e.g., concave, convex, conical, frustum).

As seen in FIG. 3, the back 14 of the earplug 10 is wider (e.g., has a larger diameter) than the front 12. As a result, the side 16 of the earplug 10, which is generally cylindrical, tapers from the back 14 toward the front 12. It is understood, however, that the side 16 of the earplug 10 can taper in the opposite direction, i.e., from the front 12 toward the back 14. It is also understood that the front 12, the back 14, and side 16 of the earplug 10 can have substantially the same width and free from tapering.

In the illustrated embodiment, a beveled edge 18 connects the front 12 and the side 16 of the earplug 10. The beveled edge 18 facilitates insertion of the earplug 10 into the ear canal of the user. As seen in FIG. 3, the beveled edge 18 of the illustrated embodiment of the earplug 10 includes a pair of angled surfaces 18a, 18b. The first angled surface 18a of the beveled edge 18, which is disposed adjacent the front 12, is wider (i.e., has a greater extent) than the second angled surface 18b. However, the second angled surface 18b, which is disposed adjacent the side 16, has a greater incline than the first angled surface 18a. It is understood, however, that the beveled edge 18 can include more or fewer angled surfaces and have other configurations (e.g., rounded, squared). A generally rounded edge 20 connects the back 14 and side 16 of the earplug 10. It is understood, that the rounded edge 20 can have other suitable configurations (e.g., squared, angled).

Figure 5:
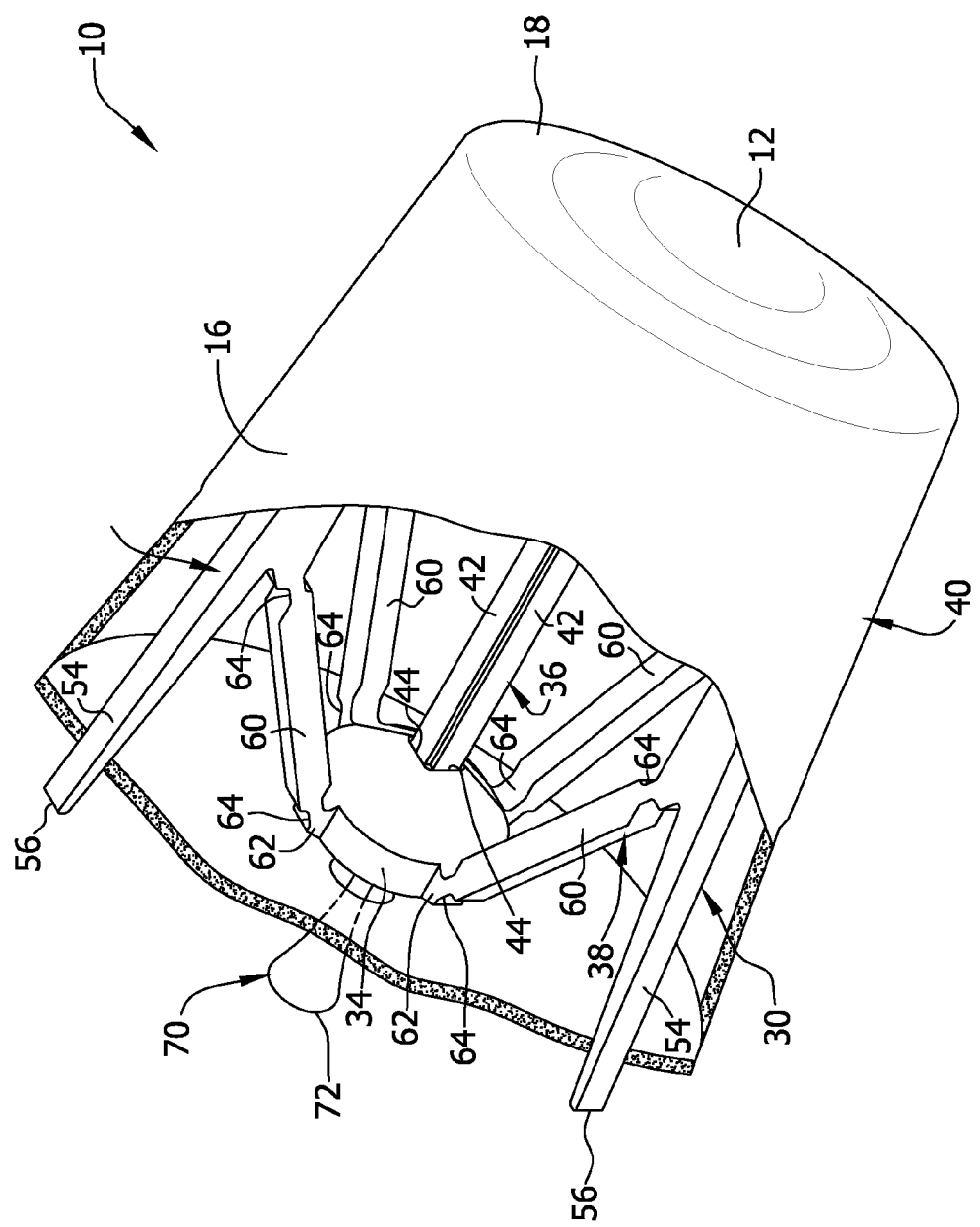
FIG. 5 is a perspective view of the earplug with a portion of a foam cover cut away to expose a portion of a resilient core structure.

With reference now to FIG. 5, the earplug 10 includes a core structure, indicated generally at 30, and a cover, indicated generally at 40, covering at least a portion of the core structure. In the illustrated embodiment, the cover 40 is a soft foam material that completely covers the core structure. Suitably, the cover 40 is pliable, soft feeling, nonirritating and otherwise adapted for direct contact with the ear canal of the user. One suitable soft foam material for use as the cover 40 is polyurethane memory foam. It is contemplated, however, that any suitable material can be used (e.g., wool, natural rubber, silicone rubber, synthetic foam, polyimide foam, neoprene rubber, polystyrene) for the cover 40.

With reference now to FIGS. 6-12, the core structure 30 comprises a resiliently deformable framework that is selectively moveable between an un-deformed position (FIG. 11) and a deformed, insertable position (FIG. 12) for insertion of the earplug 10 into the ear canal of the user. As seen in FIGS. 6-9, the core structure 30 comprises a generally cruciform first hub 32 and a generally conical second hub 34 spaced from the first hub. A shaft, indicated generally at 36, and four beam members, indicated generally at 38, extend between and connect the first and second hubs 32, 34. As used herein, the term "resilient" means that a material or a composite formed from more than one material has a property that permits it to be deformed in size and/or shape by application of a force and then to recover at least about 80% of its original size and shape after removal of the force causing the deformation.

Figure 6:
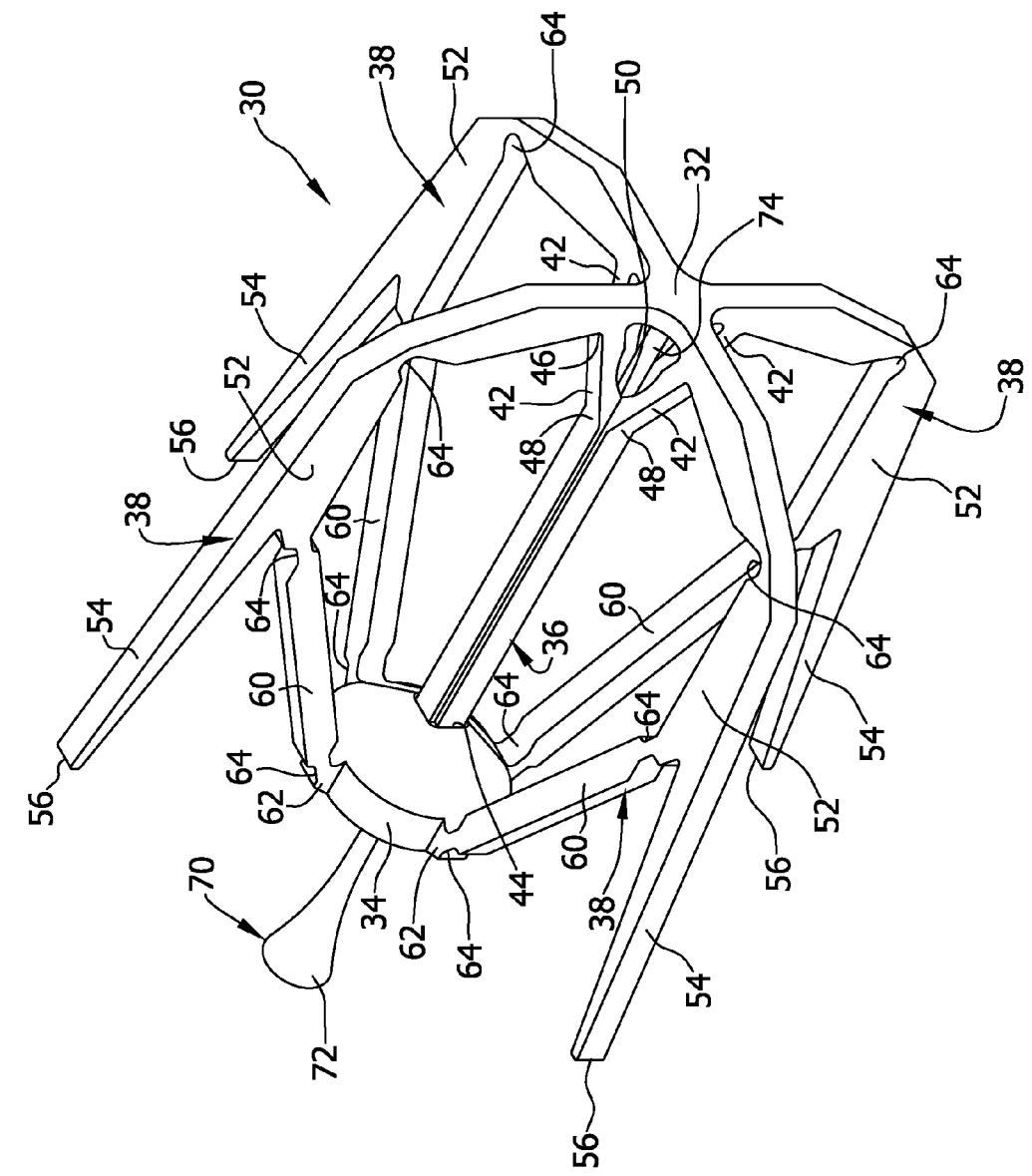
FIG. 6 is a perspective of the core structure of FIG. 5.
Figure 7:
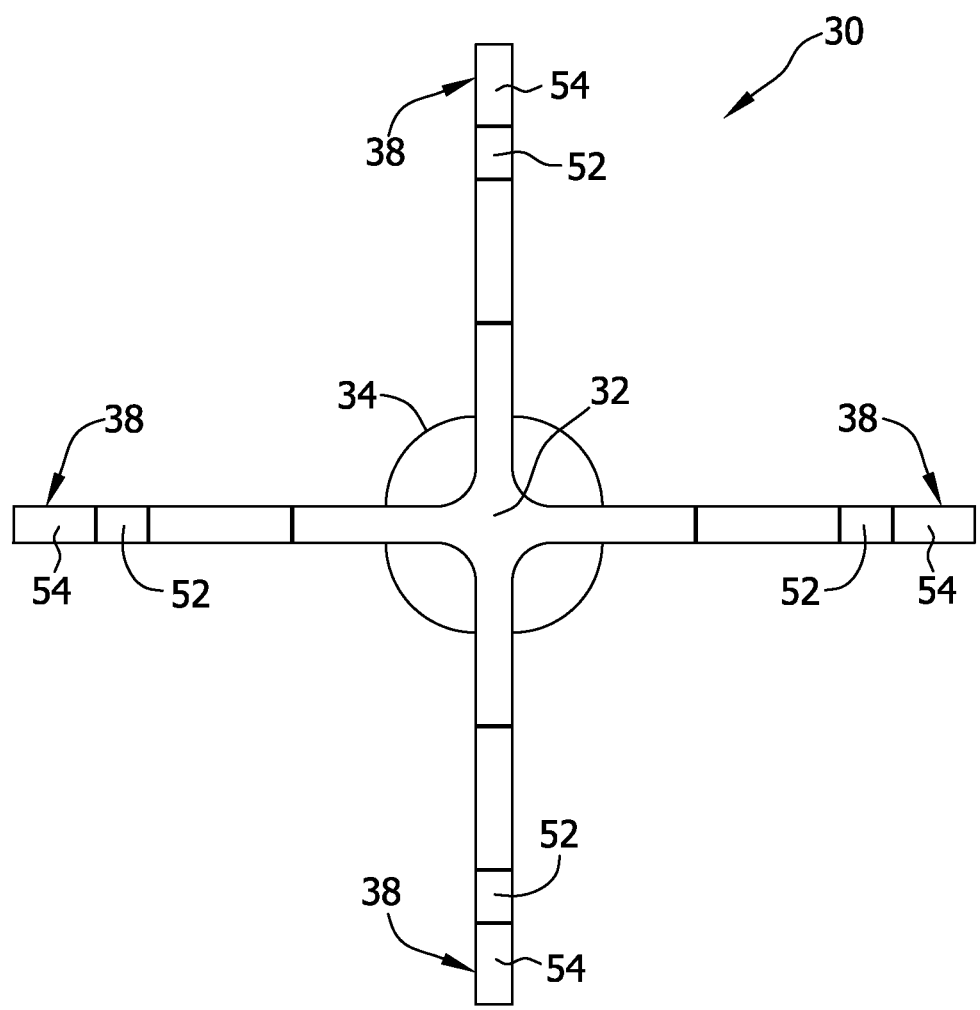
FIG. 7 is a front end view of the core structure.

As seen in FIG. 6, the shaft 36 has a first end 44 attached to the second hub 34, a second end 46 attached to the first hub 32, and a central passage 50 extending between its first and second ends. In the illustrated embodiment, the shaft 36 divides into a plurality of shaft elements 42 (e.g., four shaft elements being seen in the illustrated embodiment) about a plurality of bends 48 in the shaft. As a result, each of the shaft elements 42 are spaced apart at their respective free ends and are connected to the first hub 32 at a location spaced from the center of the first hub.

Figure 8:
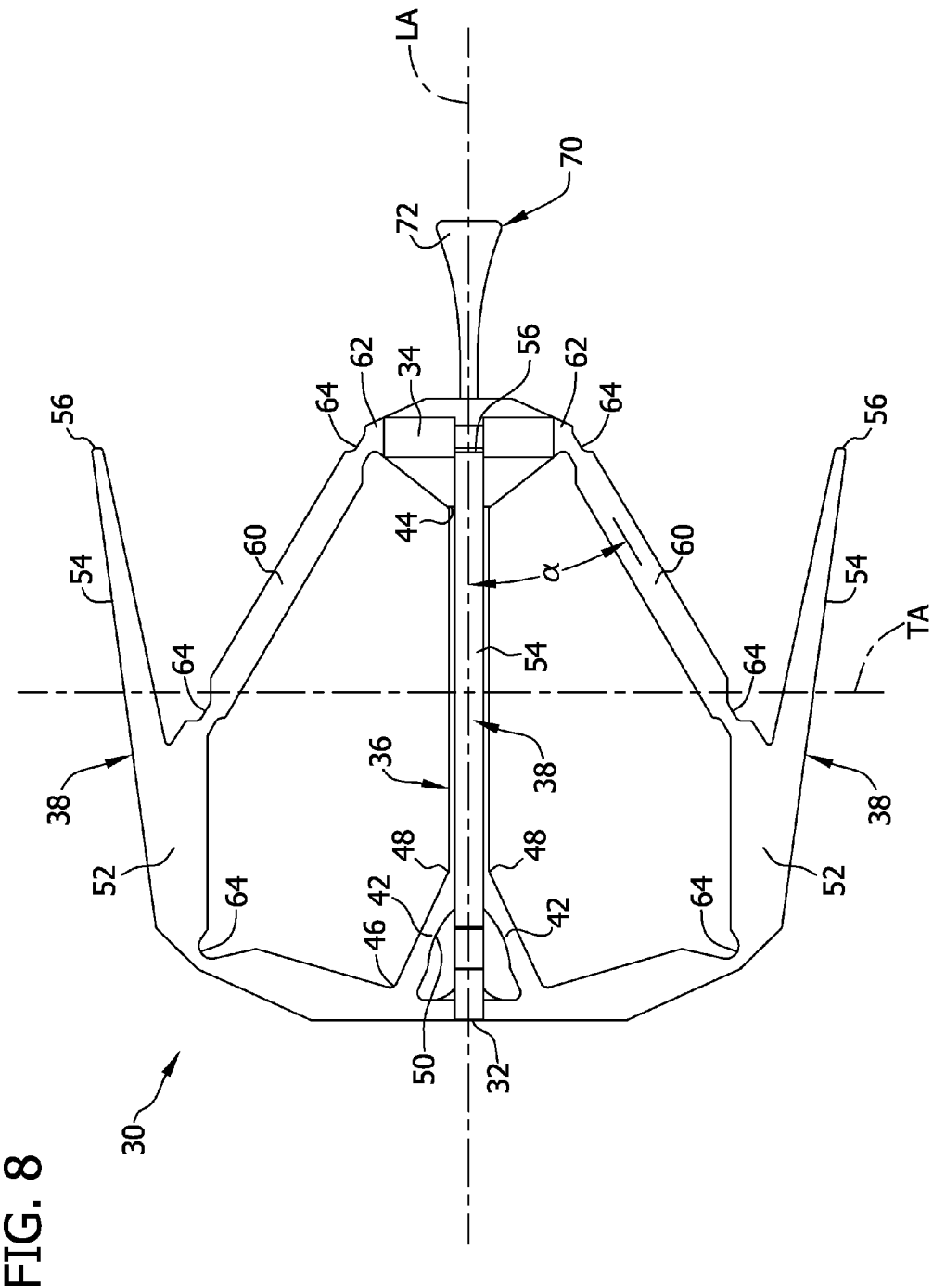
FIG. 8 is a right side view of the core structure.
Figure 9:
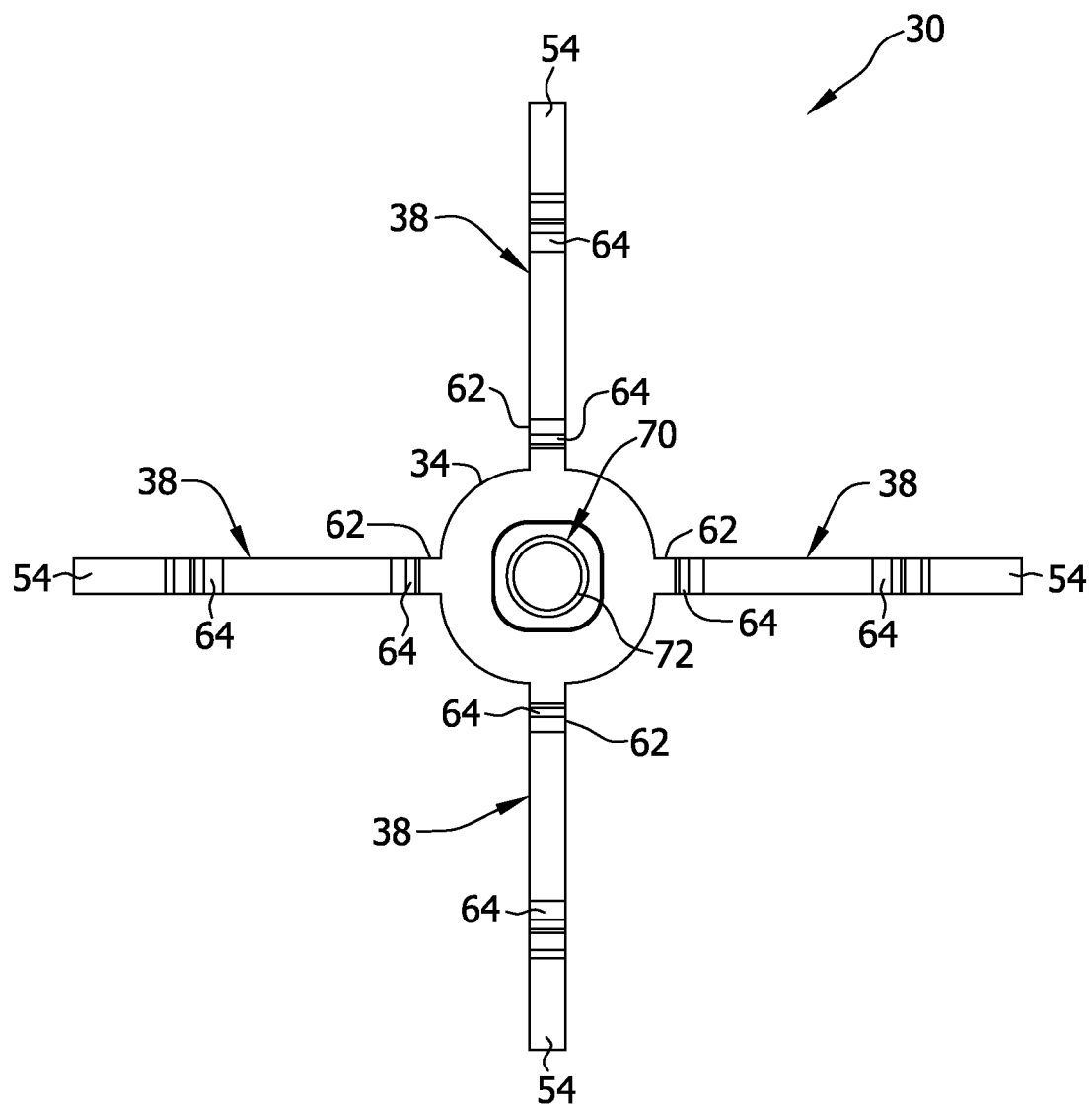
FIG. 9 is a back end view of the core structure.

Each of the four beam members 38 are substantial the same. As illustrated in FIG. 6, each of the beam members 38 comprises a first beam segment 52 extending outward from and hingedly connected to the cruciform first hub 32. Each first beam segment 52 includes a stem 54 having a free end 56 spaced from the first hub 32. The first beam segment is hingedly connected to a second beam segment 60 at a location near it center. Each of the second beam segments 60 are generally straight and lie at an angle relative to the longitudinal axis LA and transverse axis TA of the earplug 10 (FIG. 8). In the illustrated embodiment, for example, each of the second beam segments 60 lie at an angle α of approximately 45 degrees with respect to the longitudinal axis LA of the earplug 10. It is understood, however, that the second beam segments 60 can have different angles α relative to the longitudinal axis LA of the earplug 10. The second beam segments 60 are hingedly connected to respective third beam segments 62. Each of the third beam segments 62, which are relatively short, is affixed to the second hub 34.

In the illustrated embodiment, each of the hinges connecting the beam segments 52, 60, 62 is a living hinge 64 about which the respect segment can move. It is contemplated, however, that the hinges between the segments of the beam members can be other than living hinges.

In one suitable embodiment, the core structure 30 is formed (e.g., molded) from a single piece of polymeric material. Materials suitable for the forming the core structure 30 include, but are not limited to, polypropylene (PP), polyethylene terephthalate (PET), polyethylene (PE), polyvinyl, polyester, and polycarbonate. It is contemplated, however, that core structure can be made from any suitable material and can be made from two or more pieces that are joined together.

With reference again to FIG. 6, an actuator, indicated generally at 70, has a head 72 and a generally cylindrical post 74 extending outward from the head. The post 74 of the actuator 70 extends through an opening in the second hub 32 and the passage 50 of the shaft and into contact with an inner surface of the first hub 32. In the illustrated embodiment, the actuator 70 and, more specifically, the head 72 in combination with the post 74 are generally shaped like a golf tee. While it is understood that the actuator can have other shapes, the generally golf tee like shape of the illustrated actuator 70 facilitates manual manipulation of the actuator by the user.

Figure 10:
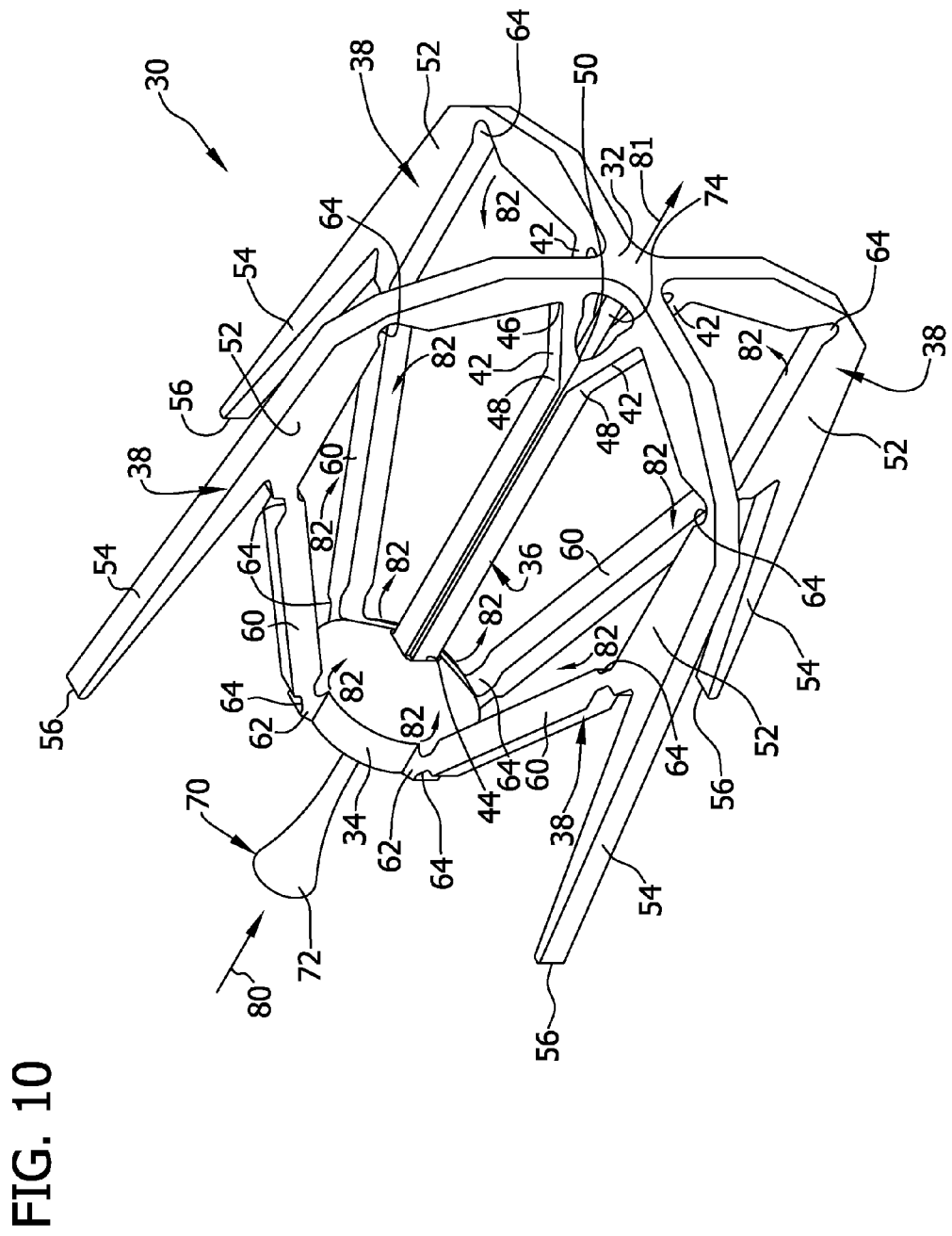
FIG. 10 is a perspective of the core structure in an un-deformed position.
Figure 11:
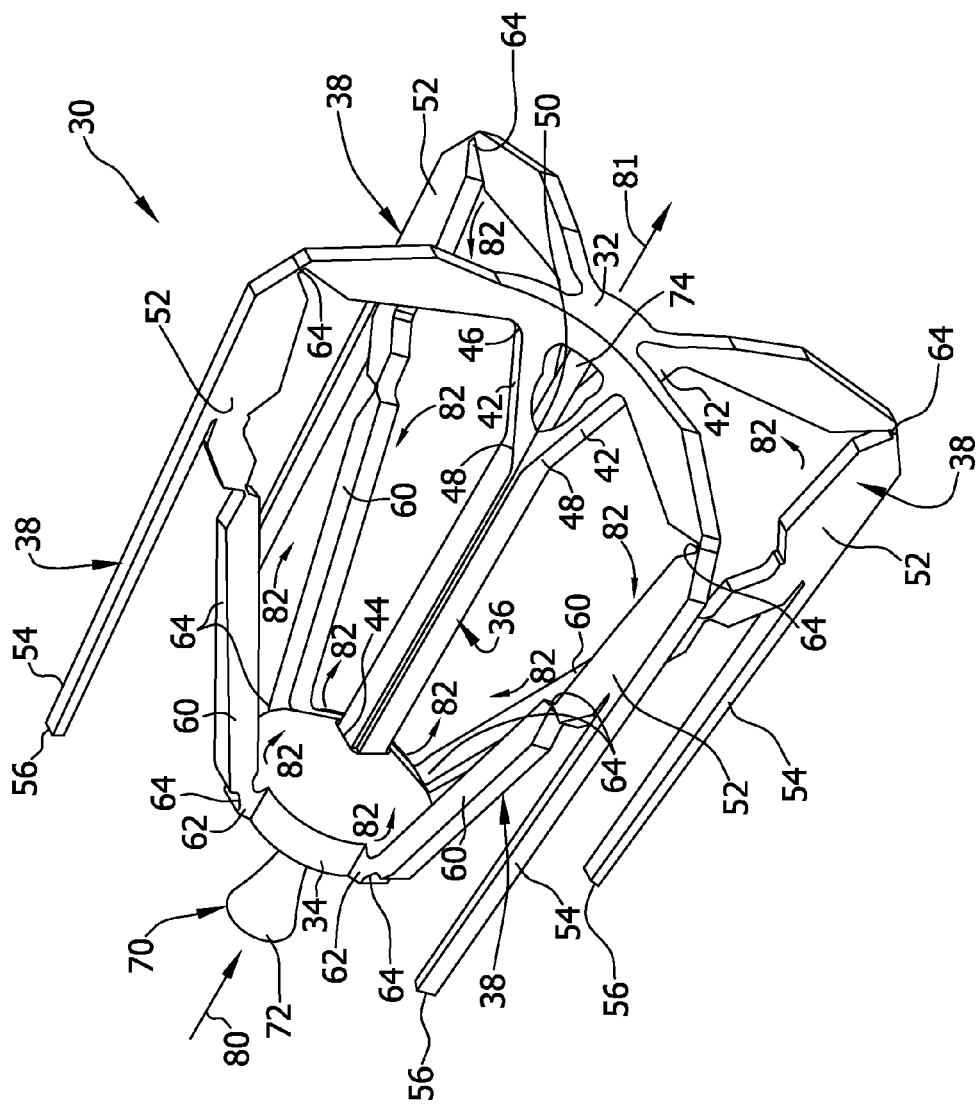
FIG. 11 is a perspective of the core structure in a deformed, insertable position.

As seen in FIGS. 10 and 11, the core structure 30 can be moved from the un-deformed position (FIG. 10) to the deformed, insertable position (FIG. 11) by application of a force generally along the longitudinal axis LA of the earplug 10 (as indicated by arrow 80 in FIGS. 10 and 11) to the actuator 70. More specifically, the user can manually apply the force, for example using a finger, to the head 72 of the actuator 70, which pushes the post 74 against the inner surface of the first hub 32. As a result, the post 74 causes the first hub 32 to bow slightly outward (i.e., in a direction of arrow 81). Bowing the first hub 32 outward causes the first and second beam segments 52, 60 to pivot inward about the living hinges 64 (as indicated by direction arrows 82) towards the shaft 36 to the deformed, insertable position. The stems 54 of the first beam segments 52 are also brought inward toward the shaft 36. Once the force applied to the actuator 70 is released, the core structure, which is resilient, will return to approximately the un-deformed position of FIG. 10.

Figure 12:
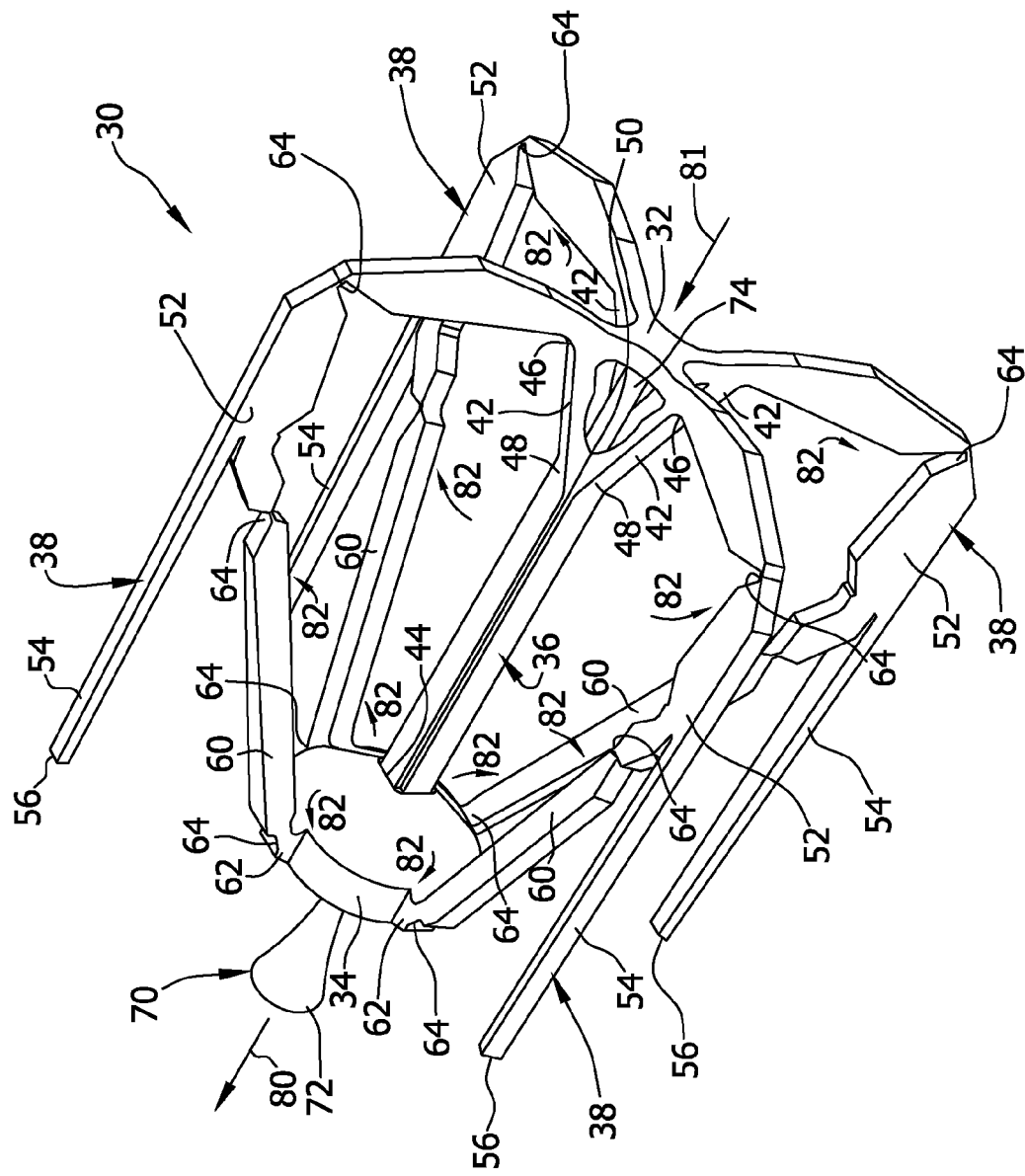
FIG. 12 is a perspective of the core structure in a deformed, inserted position.

FIG. 12 is a perspective of the core structure 30 in a deformed, inserted position. That is, FIG. 12 illustrates the position that the core structure 30 will have as inserted in the ear canal of the user. The resiliency of the core structure 30, which is trying to move the core structure back to the un-deformed position, will cause the earplug 10 to apply a force against the ear canal of the user. This force causes the earplug 10 to seal against the ear canal of the user.

Figure 13:
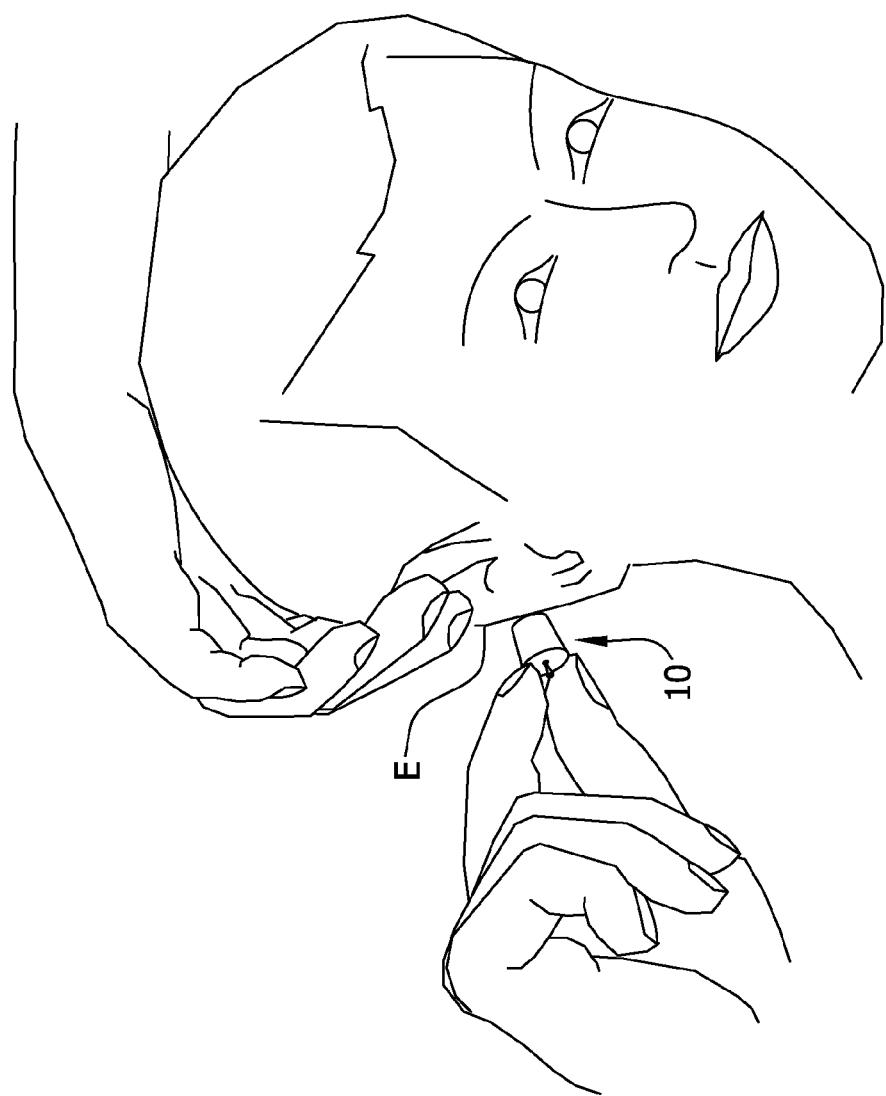
FIG. 13 is a perspective of the earplug in the un-deformed position adjacent a user's ear.
Figure 14:
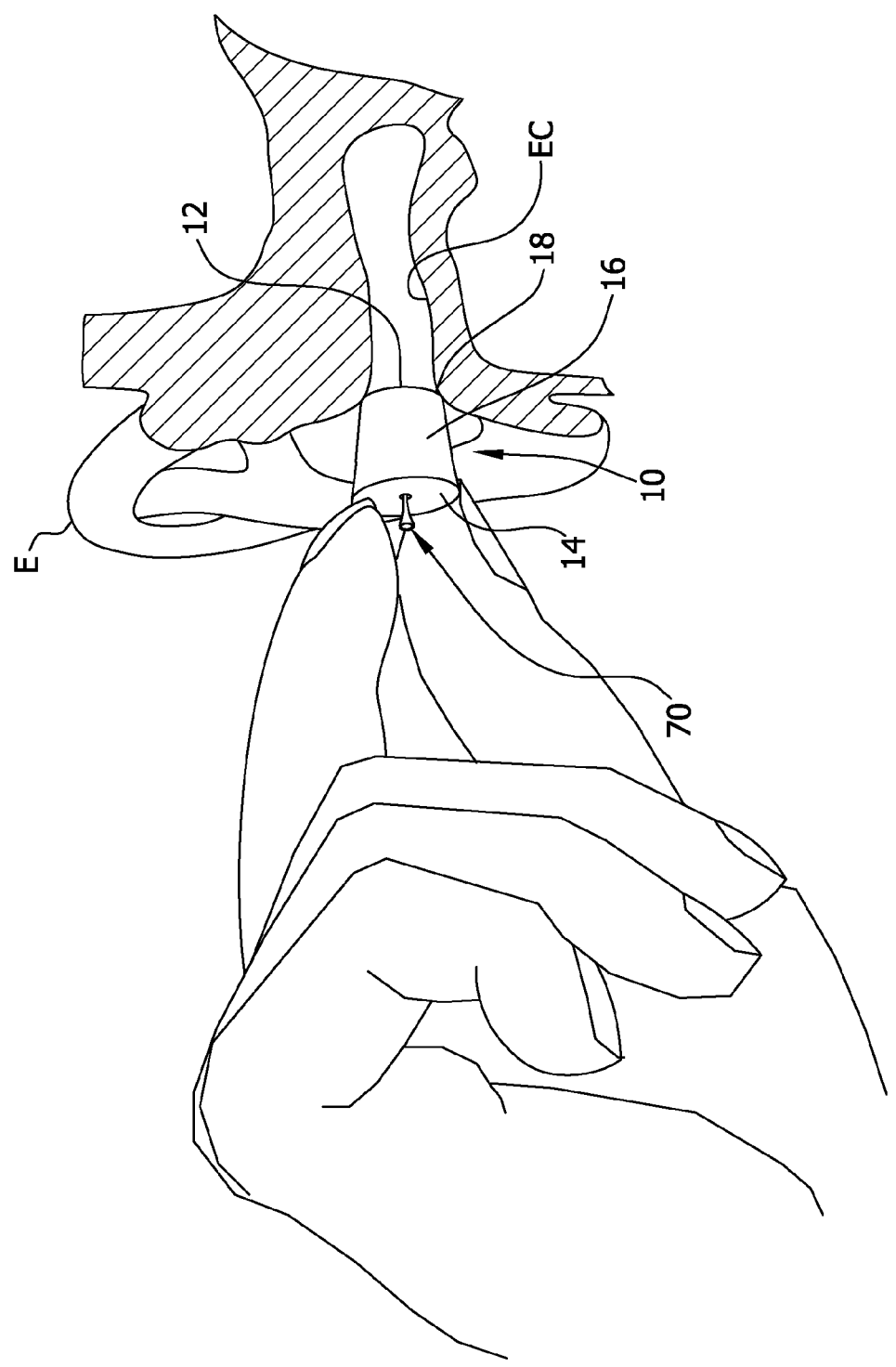
FIG. 14 is a perspective of the earplug in the deformed, insertable position being inserted into an ear canal of the user's ear.
Figure 15:
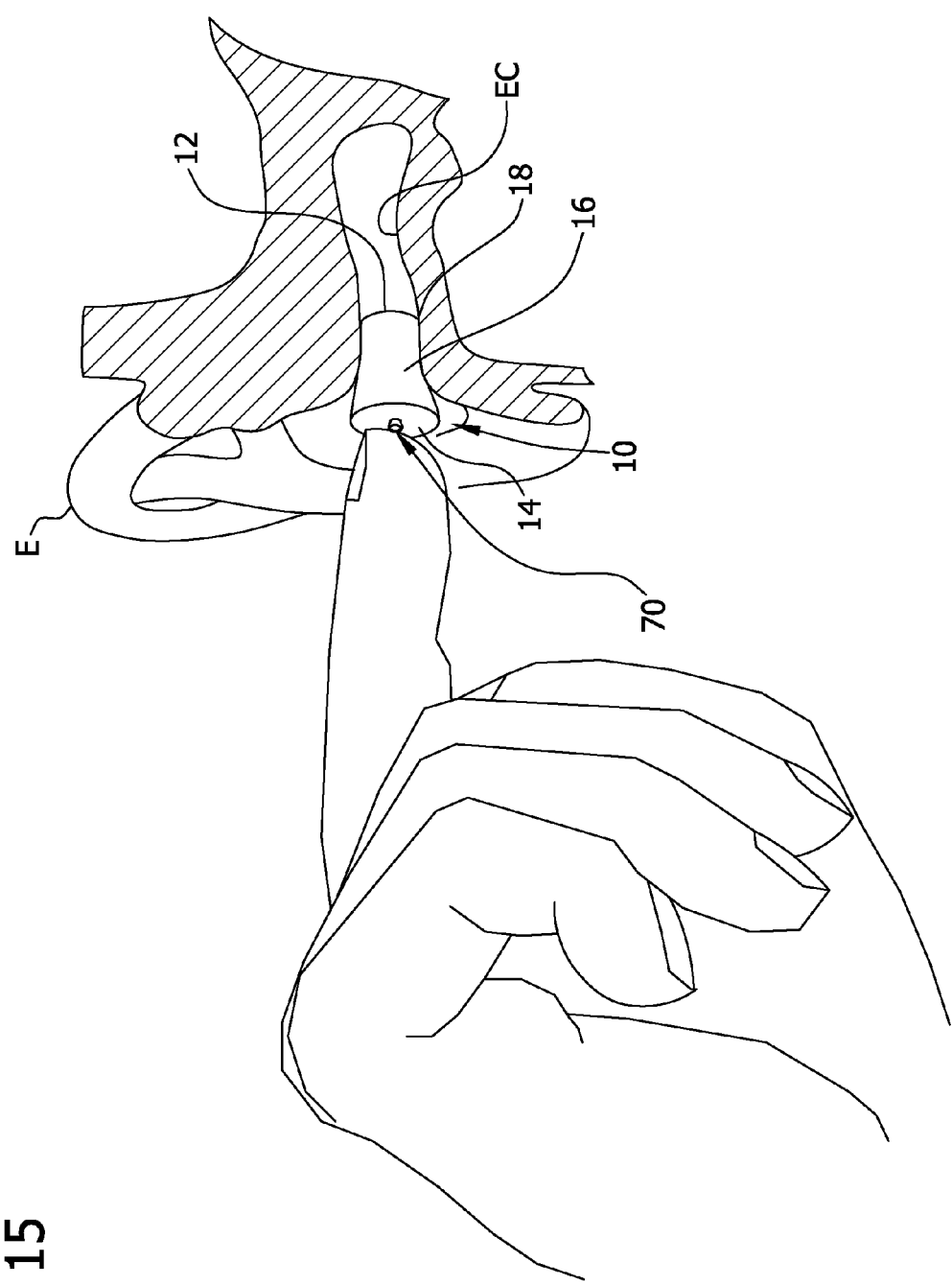
FIG. 15 is a perspective of the earplug in the deformed, insertable position inserted into the user's ear canal.

In use, as seen in FIGS. 13-16, the earplug 10 can be inserted into the ear canal EC of the ear E of the user. Particularly, FIGS. 13 and 14 illustrate the user moving the earplug 10 into engagement with an outer portion of the ear canal EC. As seen in FIG. 14, the front 12 of the earplug 10 is brought adjacent the ear canal such that the beveled edge 18 engages the ear canal opening. The user then pushes or otherwise applies a force to the actuator 70 to move the earplug 10 from the un-deformed position to the deformed, insertable position (FIG. 15). As described above, the core structure 30 collapses in the deformed, insertable position, which reduces the width of the earplug thereby making it easier to insert. With the earplug 10 in the deformed, insertable position, the user pushes the earplug into the ear canal EC of the ear to the desired depth within the ear canal as seen in FIG. 15.

Figure 16:
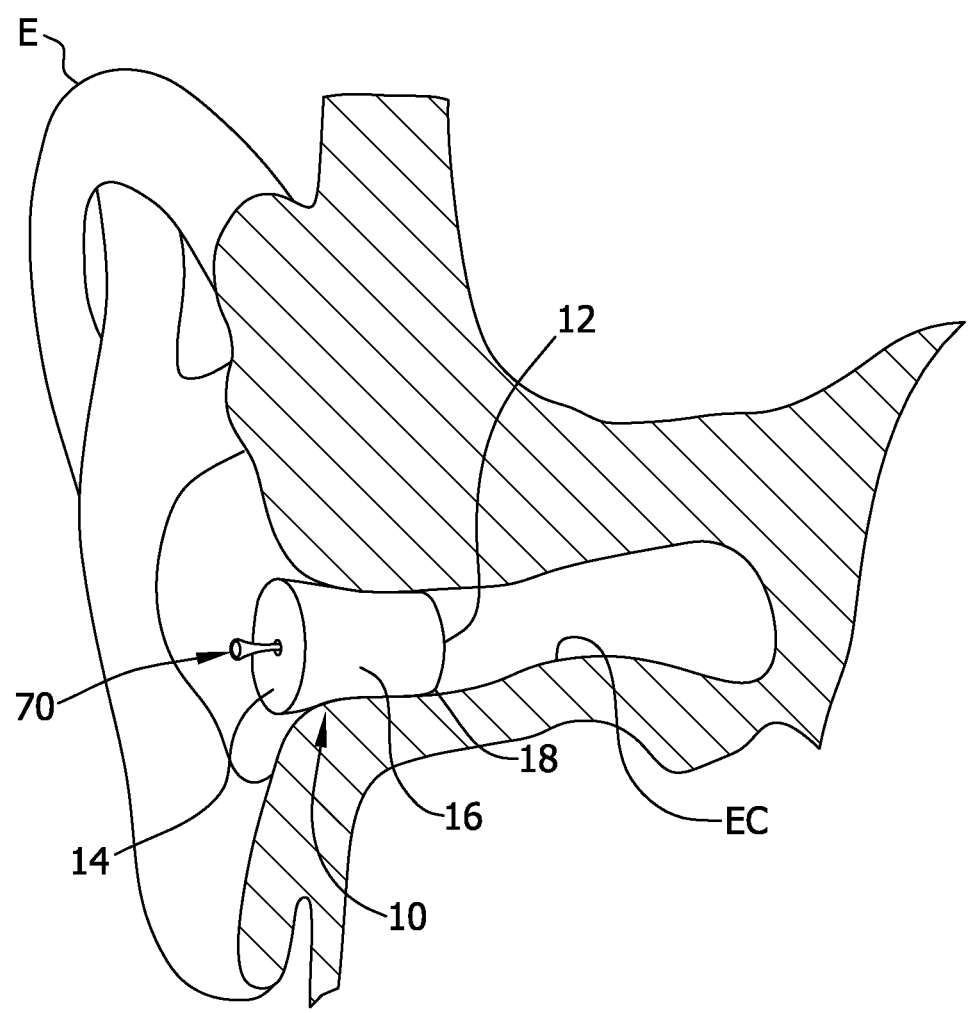
FIG. 16 is a perspective of the earplug in the deformed, inserted position wherein the earplug is sealingly engaged with the user's ear canal.
Figure 17:
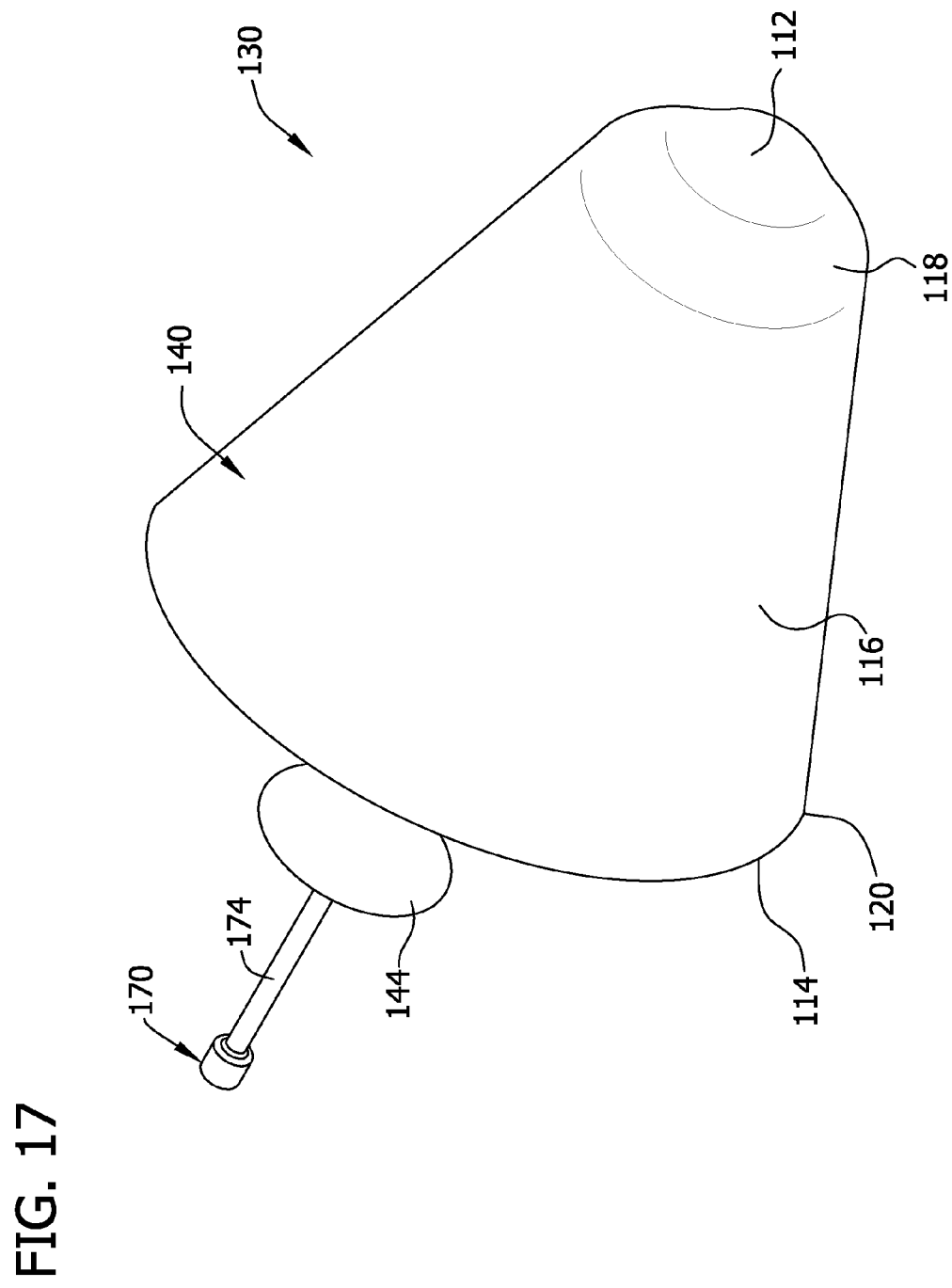
FIG. 17 is a perspective of an earplug having another suitable embodiment.
Figure 18:
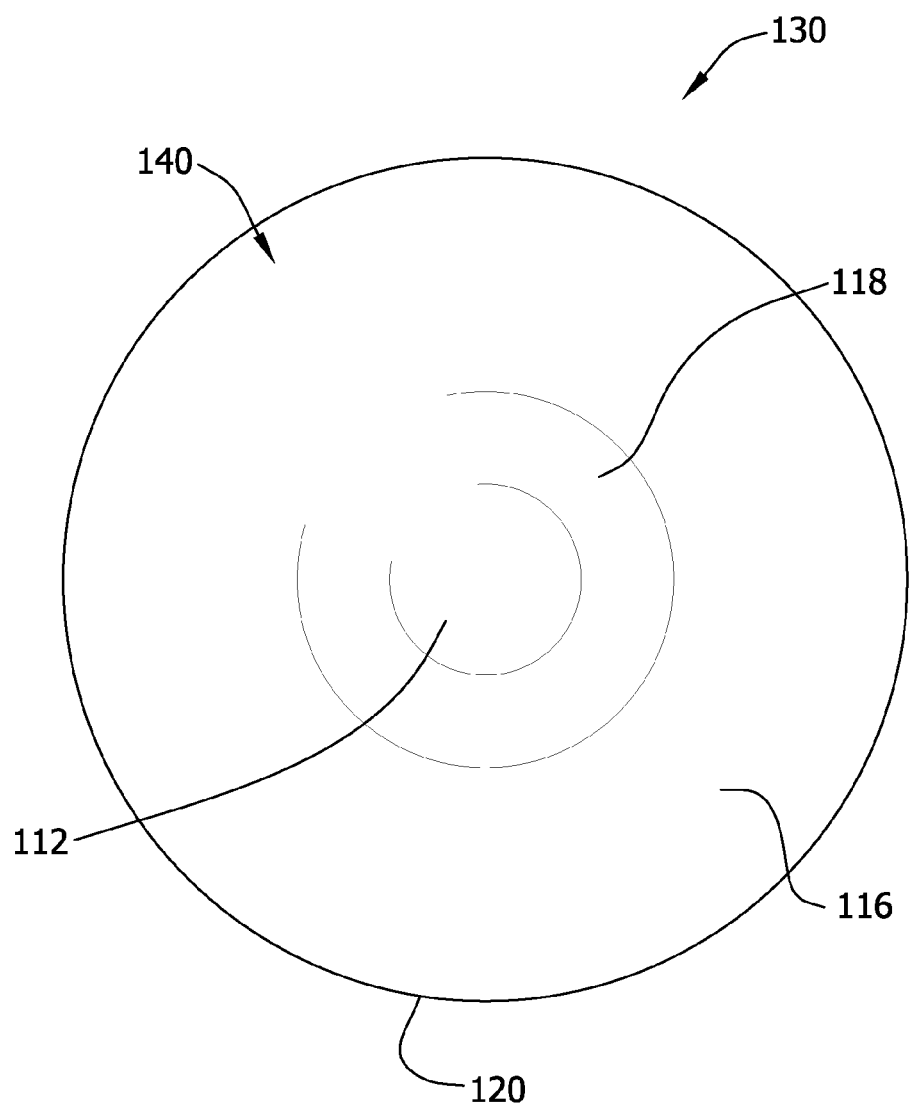
FIG. 18 is a front end view of the earplug of FIG. 17.

Once the earplug 10 is inserted to the desired depth, the user releases the actuator 70. Because of the resiliency of the core structure 30, the earplug 10 rapidly tries to return from the deformed, insertable position to the un-deformed position, which applies a force against the ear canal EC of the user as illustrated in FIG. 16. At this point, the earplug 10 is located in the ear canal EC of the user's ear E in a partially deformed, inserted position wherein the earplug is sealingly engaged with the user's ear canal. In particular, the overall shape of the earplug 10 in the partially deformed, inserted position is partially determined by the size and shape of the user's ear canal. That is, the earplug 10 at least in part conforms to the size and shape of the user's ear canal. Once inserted in the ear canal EC, the earplug 10 will reduce the effects of noise in high noise environments.

As illustrated in FIGS. 13-16, the earplug 10 can be inserted in the ear canal EC of the user without the user contacting (e.g., manually grasp or otherwise touching) the portion of the cover 40 of the earplug that is inserted. Thus, the earplug 10 can be inserted into the ear canal of the user in a hygienic manner.

FIGS. 17-28 illustrate another suitable embodiment of an earplug, indicated generally at 100, for insertion into an ear canal of a user. More specifically, the illustrated earplug 100 is configured to sealingly engage the user's ear canal and provide protection to the user against exposure to high noise levels. It is understood, however, that the earplug 100 can be adapted for use in inhibiting water, foreign bodies, dust, and/or excessive wind from entering the user's ear canal.

Figure 19:
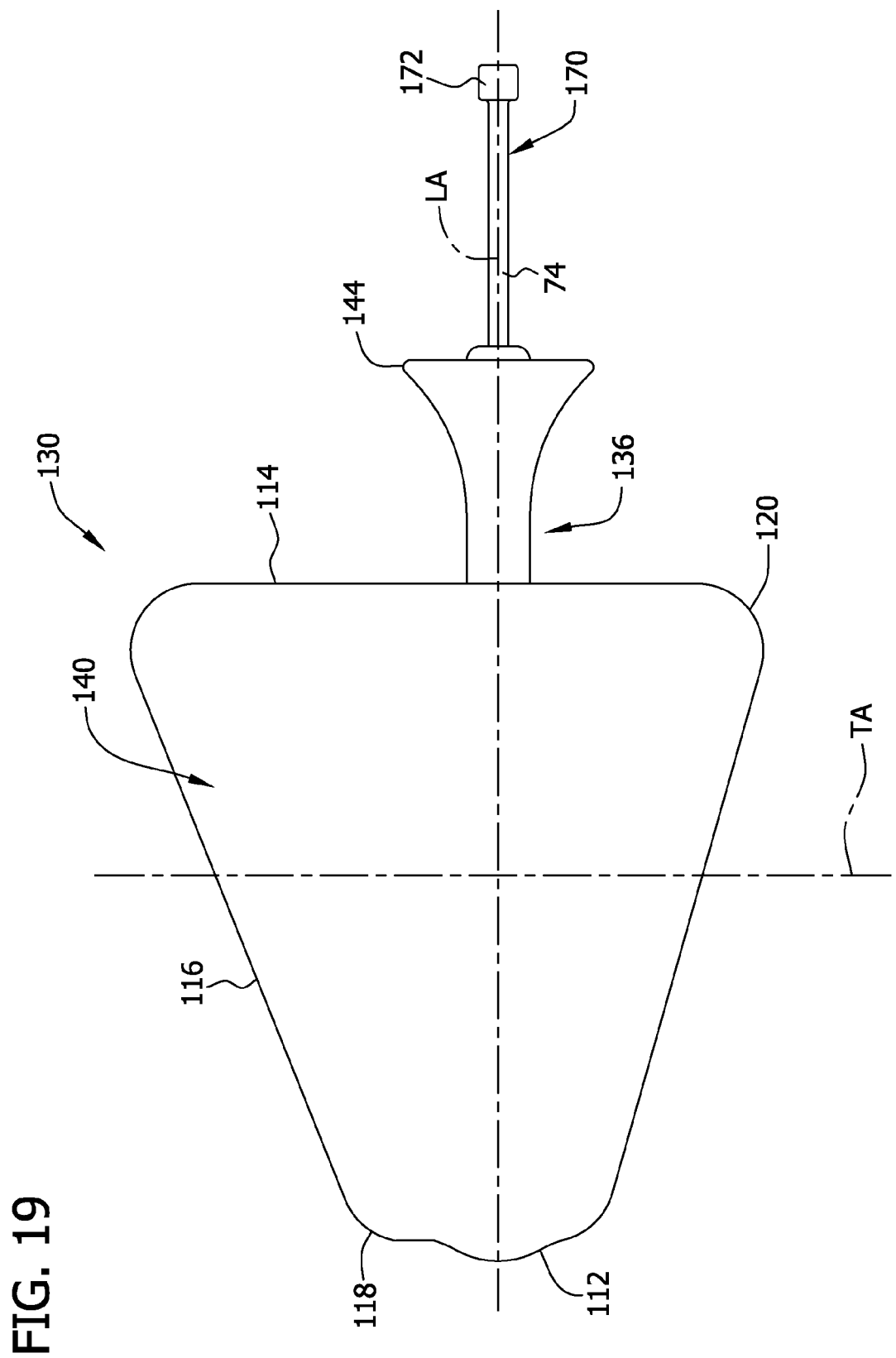
FIG. 19 is a right side view of the earplug.
Figure 20:
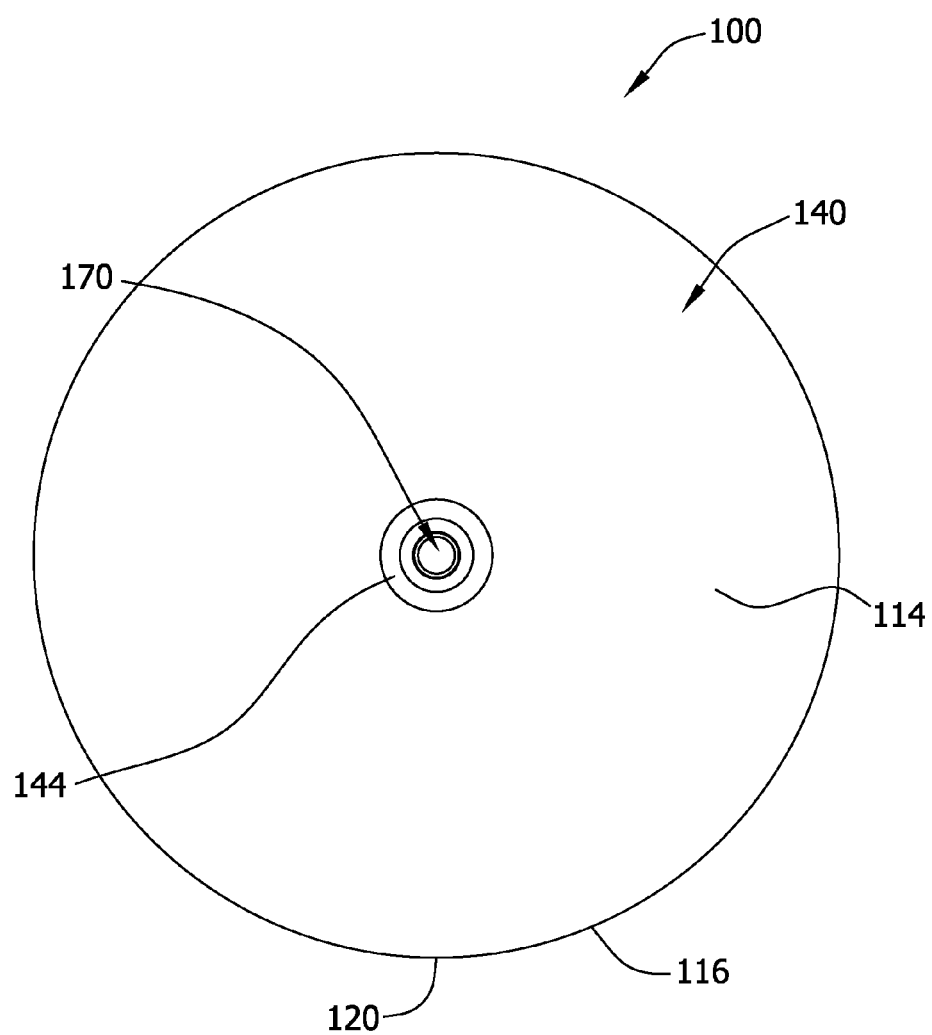
FIG. 20 is a back end view of the earplug.

The earplug 100 has a front 112, a back 114, and a side 116 extending between the front and back. The earplug 100 also has a longitudinal axis LA and a transverse axis TA (FIG. 19). In the illustrated embodiment, the front 112 of the earplug 100 is generally a hemisphere (i.e., half a sphere). It is understood, however, that the front 112 of the earplug 100 can have different configurations besides hemispherical (e.g., planar, concave, conical, frustum).

As seen in FIG. 19, the side 116 of the earplug 100 is wider (e.g., has a larger diameter) adjacent the back 114 of the earplug as compared to the width (e.g., diameter) of the side adjacent the front 112. As a result, the side 116 of the earplug 100 tapers from the back 114 toward the front 112. It is understood, however, that the side 116 of the earplug 100 can taper from the front 112 toward the back 114. It is also understood that the side 116 of the earplug 100 can have a relatively constant width along its length or, in other words, be free from tapering.

In the illustrated embodiment, a beveled edge 118 connects the front 112 and the side 116 of the earplug 100. The beveled edge 118 facilitates the insertion of the earplug 100 into the ear canal of the user. A generally rounded edge 120 connects the back 114 and side 116 of the earplug 100. It is understood, that the beveled edge 118 and rounded edge 120 can have other suitable configurations.

Figure 21:
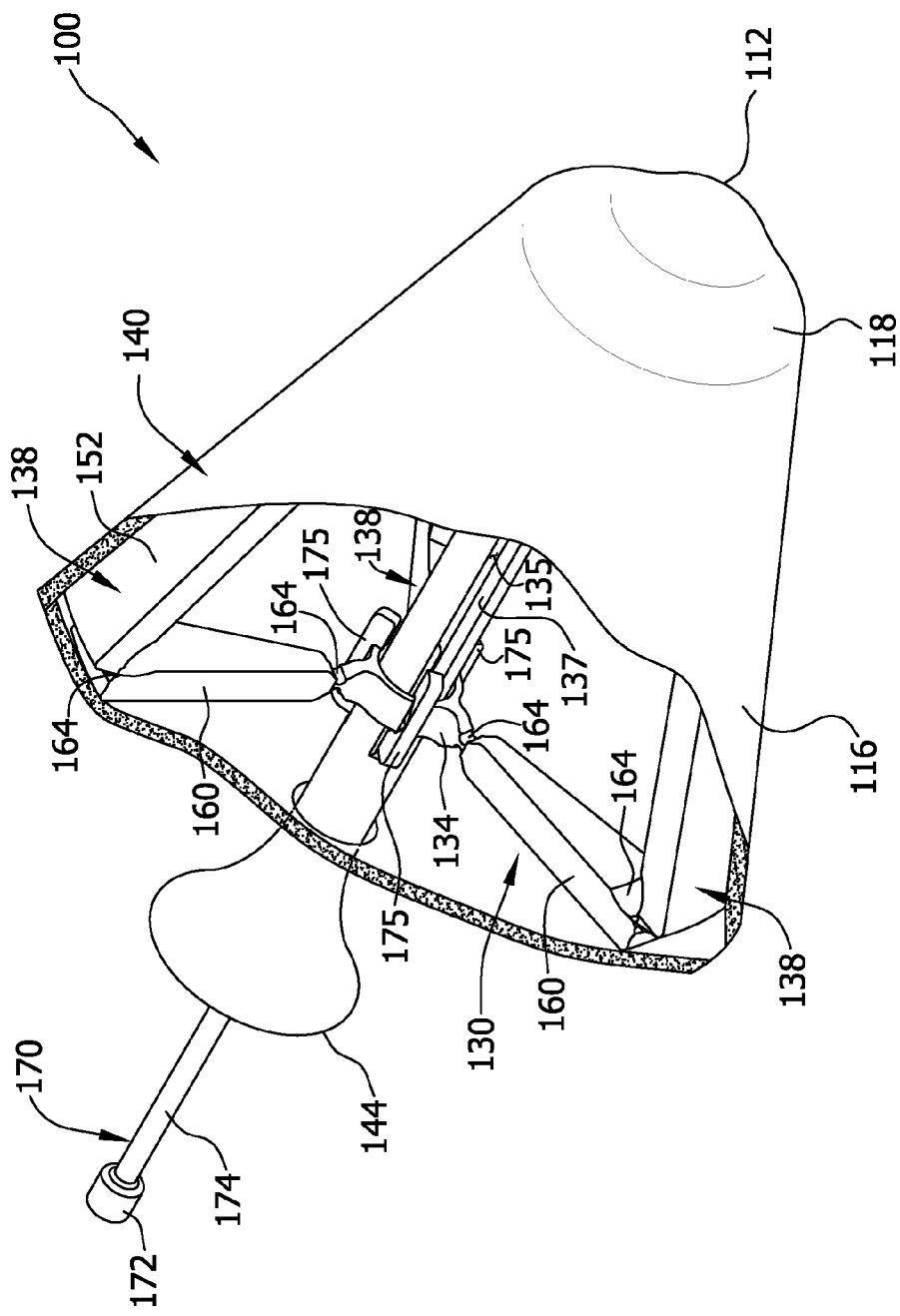
FIG. 21 is a perspective view of the earplug of FIG. 17 with a portion of a foam cover cut away to expose a portion of a resiliently deformable core structure.

With reference to FIG. 21, the earplug 100 includes a core structure, indicated generally at 130, and a cover, indicated generally at 140, covering at least a portion of the core structure. In the illustrated embodiment, the cover 140 is a soft foam material that completely covers the core structure. Suitably, the cover 140 is pliable, soft feeling, nonirritating and otherwise adapted for direct contact with the ear canal of the user.

With reference now to FIGS. 22-28, the core structure 130 comprises a resiliently deformable framework that is selectively moveable between an un-deformed position (FIGS. 22 and 26) and a deformed, insertable position (FIG. 27) for insertion of the earplug 100 into the ear canal of the user. As seen in FIGS. 22-25, the core structure 130 comprises a generally cylindrical first hub 132 and a generally tubular second hub 134 spaced from the first hub. A shaft, indicated generally at 136, extends from the first hub 132 and through a passage in the second hub 134. Three beam members, indicated generally at 138, extend between and connect the first and second hubs 132, 134.

Figure 22:
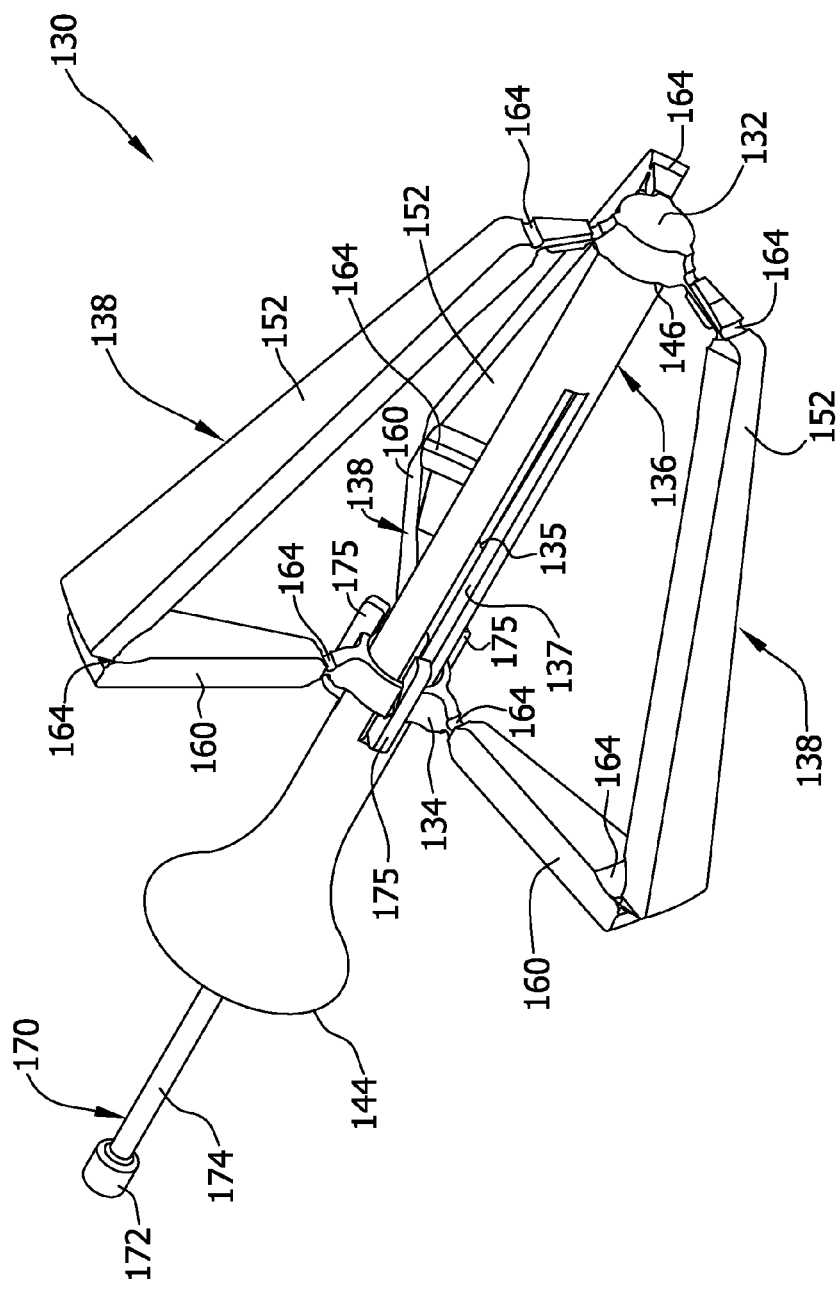
FIG. 22 is a perspective of the core structure of FIG. 21.
Figure 23:
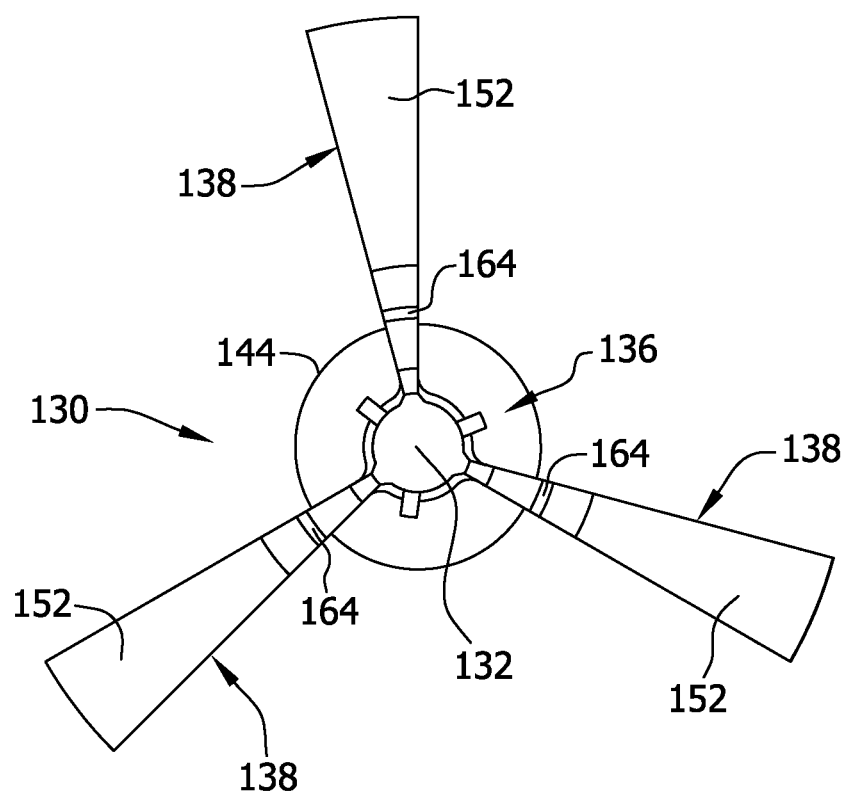
FIG. 23 is a front end view of the core structure.

In the illustrated embodiment, the shaft 136 has a generally bulbous first end 144 that is spaced outward from the second hub 134 and a second end 146 attached to the first hub 312. As seen in FIG. 22, the shaft 136 includes a passage 135 and three longitudinal slots 137 (only one slot being shown in FIG. 22) in communication with the passage.

Figure 24:
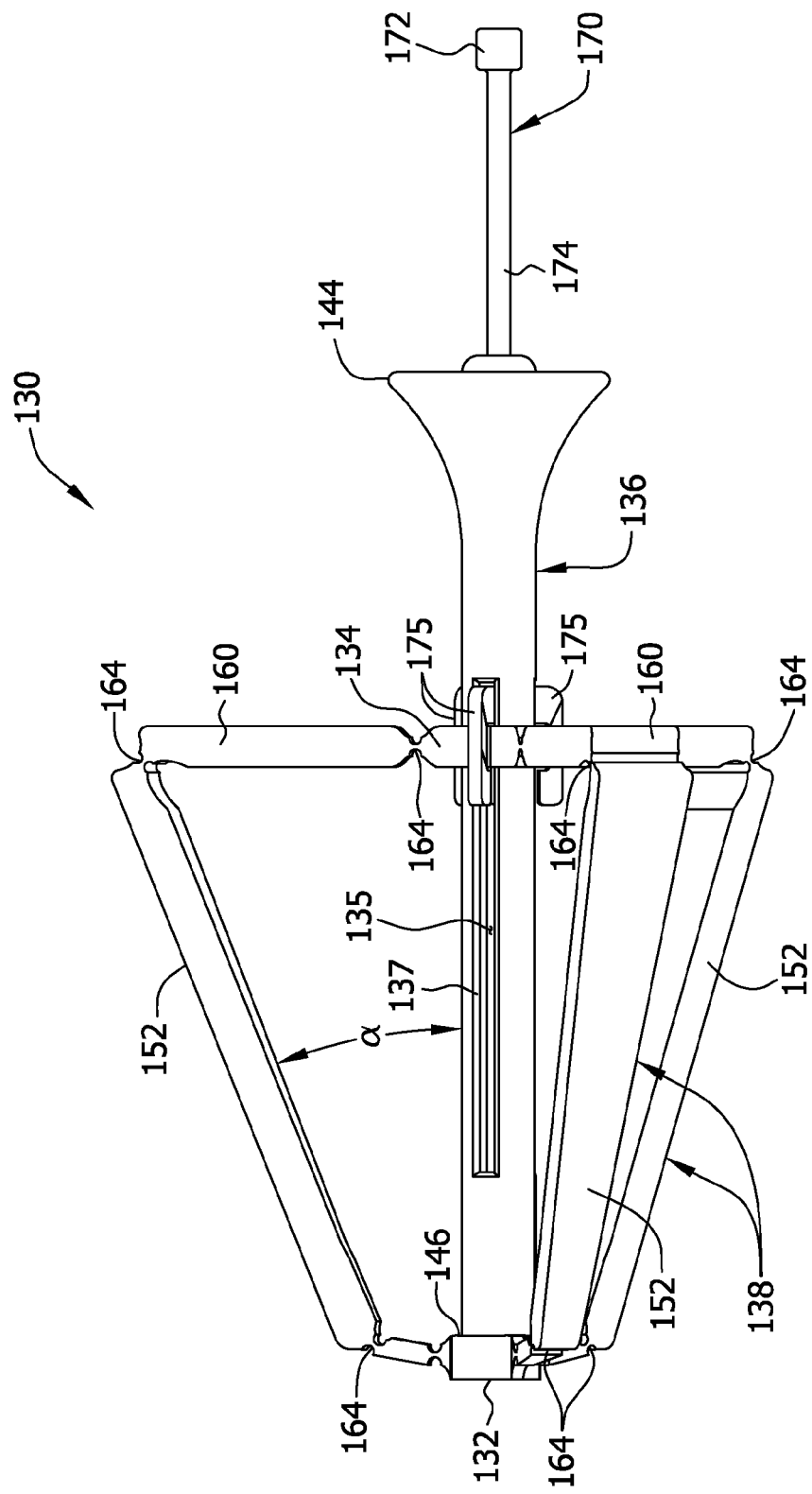
FIG. 24 is a right side view of the core structure.
Figure 25:
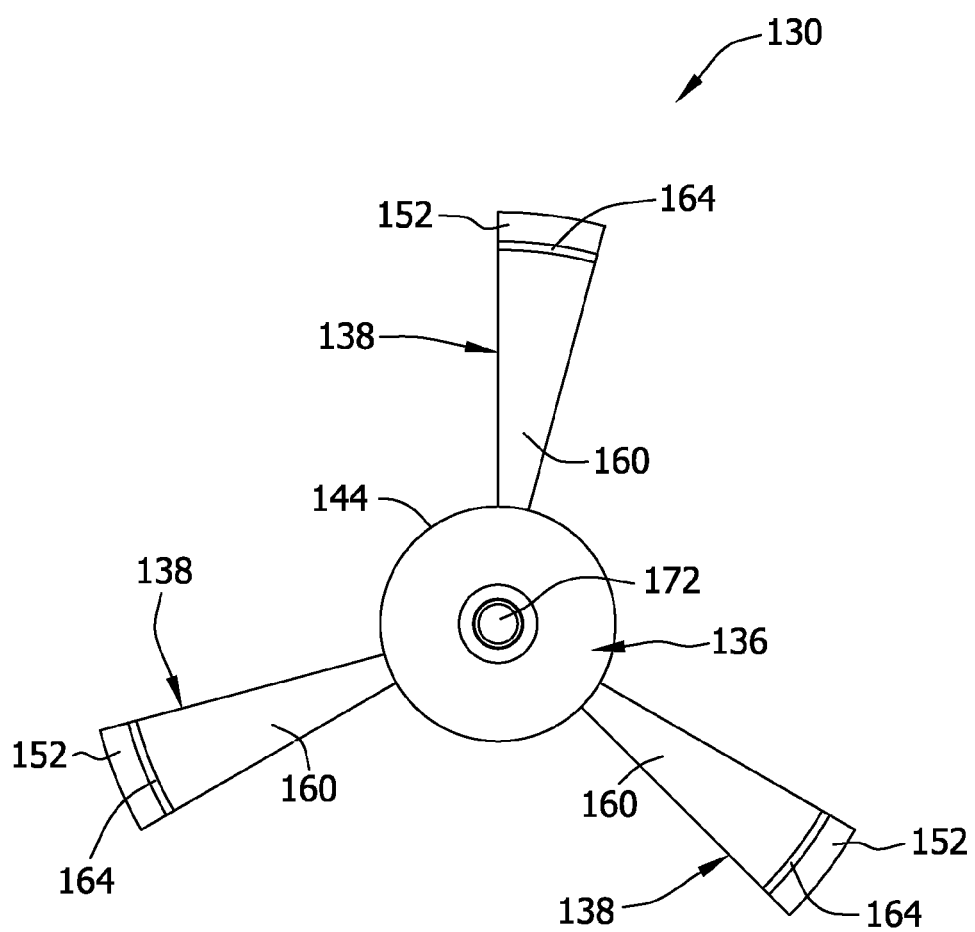
FIG. 25 is a back end view of the core structure.
Figure 26:
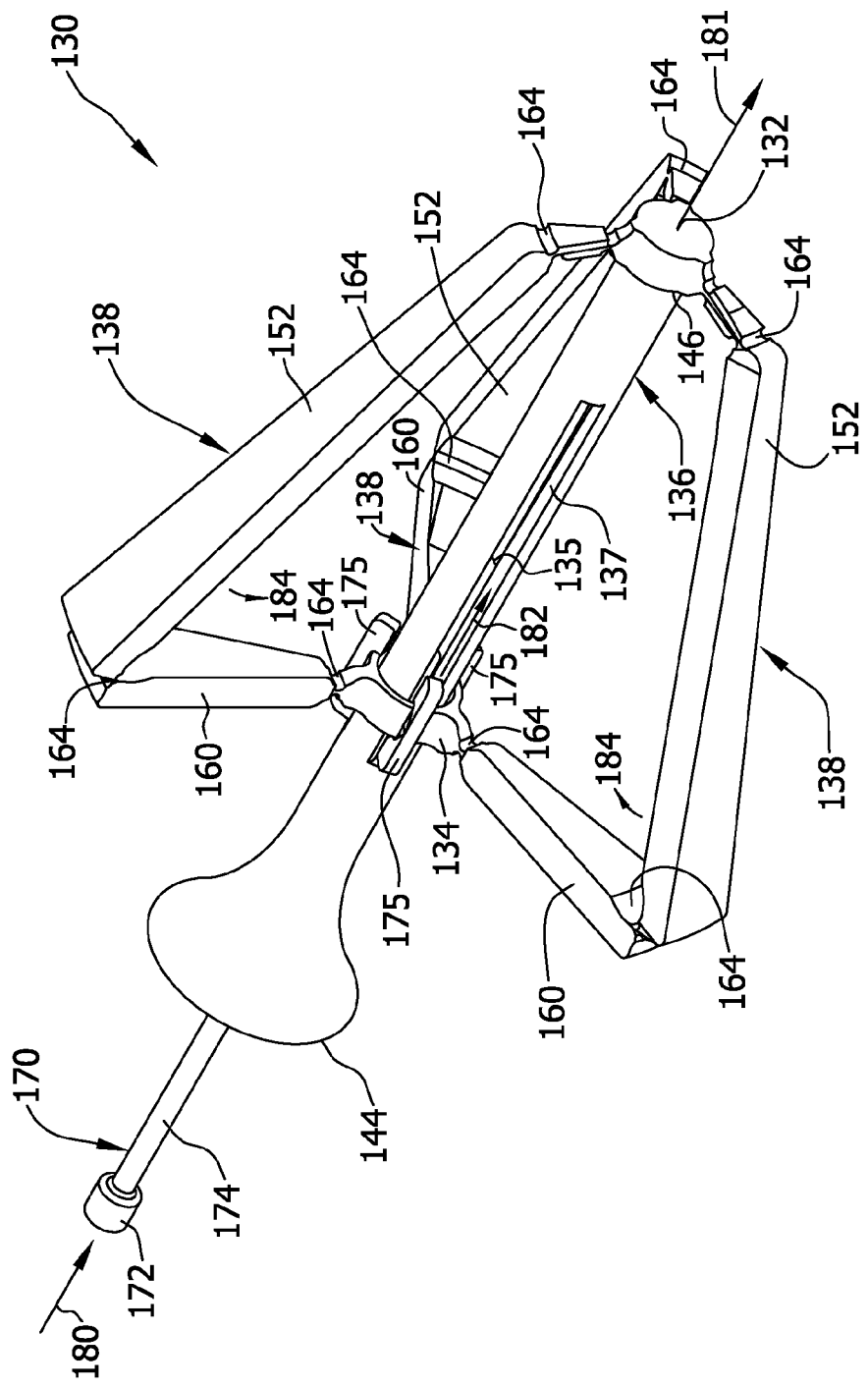
FIG. 26 is a perspective of the core structure in an un-deformed position.

Each of the three beam members 138 are substantial the same and comprises a first beam segment 152 extending outward from and hingedly connected to the first hub 132. Each first beam segments 152 is generally straight and lies at an angle α relative to the longitudinal axis LA of the earplug 10 (FIG. 24). The first beam segment 152 is hingedly connected to a second beam segment 160 at its end spaced from the first hub 132. Each of the second beam segments 160, which are generally straight, is hingedly connected to the second hub 34.

In the illustrated embodiment, each of the hinges connecting the beam segments 152, 160 is a living hinge 164 about which the respect segments can move. It is contemplated, however, that the hinges between the segments of the beam members can be other than living hinges.

An actuator, indicated generally at 170, has a head 172, a generally cylindrical post 174 extending outward from the head, and three fins 175 connected to the post. The post 174 of the actuator 170 extends into the passage 135 of the shaft 136 and each of the fins 175 extend through one of the slots 137 in the shaft 136 and operatively connect the actuator 170 to the second hub 132.

The core structure 130 can be moved from the un-deformed position (FIG. 26) to the deformed, insertable position (FIG. 27) by application of a force generally along the longitudinal axis LA of the earplug 100 (as indicated by arrow 180 in FIG. 26) to the actuator 170. More specifically, the user can manually apply the force, for example using a finger, to the head 172 of the actuator 170, which pushes the post 174. As a result, the post 174 moves within the passage 135 of the shaft 136 towards the first hub 132. Movement of the post 174 causes the fins 175 and the second hub 134, which are connected to the fins through the slots 137 in the shaft 136, to also move toward the first hub 132, as indicated by arrow 182.

Figure 27:
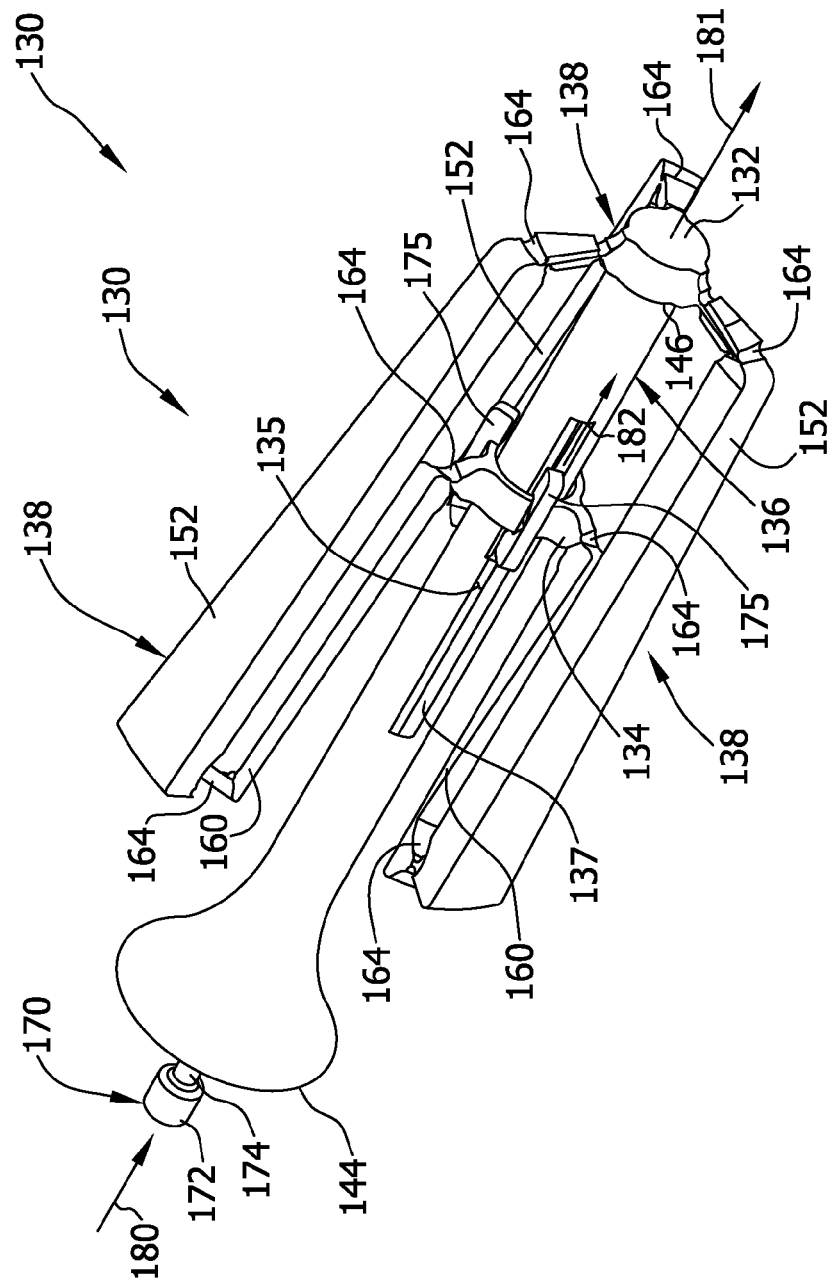
FIG. 27 is a perspective of the core structure in a deformed, insertable position.

As seen in FIG. 27, the movement of the second hub 134 causes the first and second beam segments 152, 160 to pivot inward about the living hinges 164 (as indicated by direction arrows 184) towards the shaft 136 to the deformed, insertable position. Once the force applied to the actuator 170 is released, the core structure 130, which is resilient, will return to approximately the un-deformed position of FIG. 26.

Figure 28:
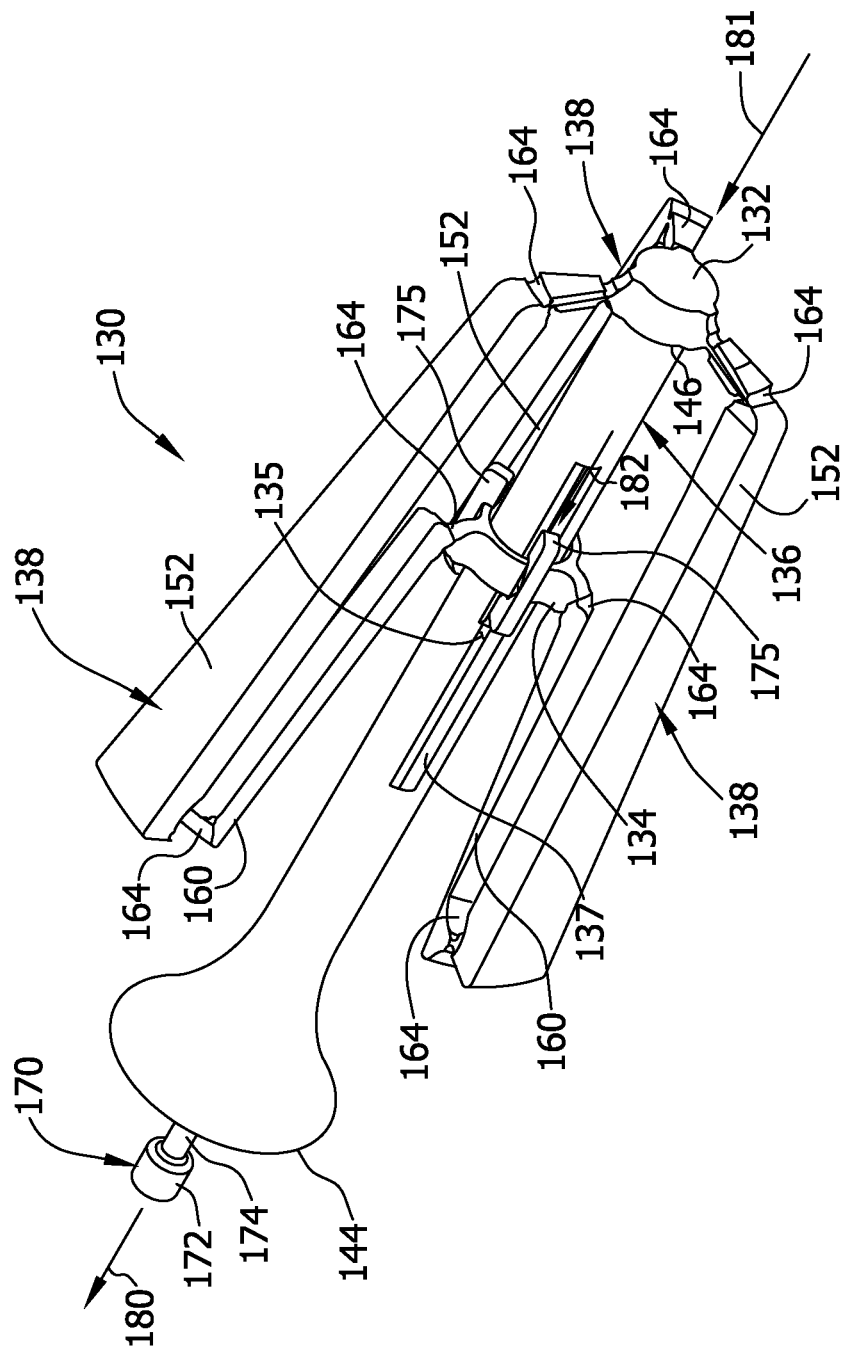
FIG. 28 is a perspective of the core structure in a deformed, inserted position.

FIG. 28 is a perspective of the core structure 130 in a deformed, inserted position. That is, FIG. 28 illustrates the position that the core structure 130 will have when inserted in the ear canal of the user. The resiliency of the core structure 130, which is trying to move the core structure to the un-deformed position, will cause the earplug 100 to apply a force against the ear canal of the user. This force causes the earplug 100 to seal against the ear canal of the user. Once inserted in the ear canal EC, the illustrated earplug 100 will reduce the effects of noise in high noise environments.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An earplug for insertion into an ear canal of a user, the earplug comprising:
   a front, a back, a side extending between the front and the back, a longitudinal axis, and a transverse axis,
   a core structure being selectively moveable from an un-deformed position to a deformed, insertable position suitable for insertion of the earplug into the ear canal of the user;
   a cover for covering at least a portion of the core structure, the cover being adapted for contact with the ear canal of the user; and
   an actuator extending outward from the back and operatively connected to the core structure for moving the core structure from the un-deformed position to the deformed, insertable position upon application of a longitudinal force to the actuator generally along the longitudinal axis.

2. The earplug as set forth in claim 1 wherein the side tapers from the back toward the front.

3. The earplug as set forth in claim 1 wherein the cover is a soft foam material that completely covers the core structure.

4. An earplug for insertion into an ear canal of a user, the earplug comprising:
   a front, a back, a side extending between the front and the back, a longitudinal axis, and a transverse axis,
   a core structure being selectively moveable from an un-deformed position to a deformed, insertable position suitable for insertion of the earplug into the ear canal of the user, the core structure being resiliently deformable such that the core structure is biased toward the un-deformed position when in the deformed, insertable position;
   a cover for covering at least a portion of the core structure, the cover being adapted for contact with the ear canal of the user; and
   an actuator extending outward from the back and operatively connected to the core structure for moving the core structure from the un-deformed position to the deformed, insertable position upon application of a force to the actuator generally along the longitudinal axis.

5. An earplug for insertion into an ear canal of a user, the earplug comprising:
   a front, a back, a side extending between the front and the back, a longitudinal axis, and a transverse axis,
   a core structure being selectively moveable from an un-deformed position to a deformed, insertable position suitable for insertion of the earplug into the ear canal of the user, wherein the core structure comprises a plurality of beam members, at least some of the beam members being connected by hinges about which the beam members can be moved;
   a cover for covering at least a portion of the core structure, the cover being adapted for contact with the ear canal of the user; and
   an actuator extending outward from the back and operatively connected to the core structure for moving the core structure from the un-deformed position to the deformed, insertable position upon application of a longitudinal force to the actuator generally along the longitudinal axis.

6. The earplug as set forth in claim 5 wherein the hinges connecting the beam members are living hinges.

7. An earplug for insertion into an ear canal of a user, the earplug comprising:
   a front, a back, a side extending between the front and the back, a longitudinal axis, and a transverse axis,
   a core structure being selectively moveable from an un-deformed position to a deformed, insertable position suitable for insertion of the earplug into the ear canal of the user, the core structure being resilient such that the core structure is biased toward the un-deformed position when in the deformed, insertable position;

a cover for covering at least a portion of the core structure, the cover being adapted for contact with the ear canal of the user; and an actuator operatively connected to the core structure for moving the core structure from the un-deformed position to the deformed, insertable position, wherein the core structure collapses to reduce a width of the earplug, upon application of a longitudinal force to the actuator.

8. The earplug as set forth in claim 7 wherein the cover comprise a foam material.

9. An earplug for insertion into an ear canal of a user, the earplug comprising:

a front, a back, a side extending between the front and the back, a longitudinal axis, and a transverse axis, a core structure being selectively moveable from an un-deformed position to a deformed, insertable position suitable for insertion of the earplug into the ear canal of the user, the core structure being resilient such that the core structure is biased toward the un-deformed position when in the deformed, insertable position, wherein the core structure comprises a framework comprising a first hub, a second hub spaced from the first hub, and a plurality of beam members extending between and connecting the first and second hubs, each of the plurality of beam members being moveable about a hinge;

a cover for covering at least a portion of the core structure, the cover being adapted for contact with the ear canal of the user; and an actuator operatively connected to the core structure for moving the core structure from the un-deformed position to the deformed, insertable position upon application of a longitudinal force to the actuator.

10. The earplug as set forth in claim 9 further comprising a shaft extending between the first and second hubs.

11. The earplug as set forth in claim 10 wherein the actuator comprises a post, and the shaft defines a passage, the post of the actuator extending into the passage of the shaft.

12. The earplug as set forth in claim 11 wherein the second hub is operatively connected to the post of the actuator and moveable with the post relative to the shaft.

13. The earplug as set forth in claim 11 wherein the post of the actuator acts on the first hub to move the core structure from the un-deformed position to the deformed, insertable position.

14. The earplug as set forth in claim 9 wherein each of plurality of beam members comprising a first beam segment and a second beam segment hingedly connected to the first beam segment by the hinge.

15. The earplug as set forth in claim 14 wherein the hinge connecting the first and second beam segments is a living hinge.

16. A method of inserting an earplug into an ear canal of an ear, the method comprising:

applying a force to an actuator of the earplug to move a core structure of the earplug from an un-deformed position to a deformed, insertable position wherein the core structure collapses to reduce a width of the earplug, the core structure being resiliently biased from the deformed, insertable portion toward the un-deformed position;

inserting the earplug into the ear canal while the earplug is in the deformed, insertable position;

releasing the actuator to move the core structure from the deformed, insertable position to a partially deformed, inserted position wherein the earplug engages the user's ear canal.

17. The method as set forth in claim 16 wherein applying a force to the actuator comprises applying a force to the actuator generally along a longitudinal axis of the earplug.

18. The method as set forth in claim 17 wherein the actuator comprises a head and a post extending outward from the head, and wherein applying a force to the actuator generally along the longitudinal axis of the earplug comprises applying the force to the head of the actuator.

19. The method as set forth in claim 16 wherein the earplug is adapted to reduce the effects of noise in high noise environments when engaged with the user's ear canal.

20. A method of inserting an earplug into an ear canal of an ear, the method comprising:

applying a force to an actuator of the earplug to move a core structure of the earplug from an un-deformed position to a deformed, insertable position wherein the core structure collapses to reduce a width of the earplug, the core structure being resiliently biased from the deformed, insertable portion toward the un-deformed position, wherein the core structure comprises a first hub, a second hub spaced from the first hub, and a plurality of beam members extending between the first and second hubs, each of the plurality of beam members having a hinge about which the beam member can be moved, wherein applying a force to the actuator causes each of the plurality of beam members to pivot about the hinge when the core structure is moved from the un-deformed position to the deformed, insertable position;

inserting the earplug into the ear canal while the earplug is in the deformed, insertable position;

releasing the actuator to move the core structure from the deformed, insertable position to a partially deformed, inserted position wherein the earplug engages the user's ear canal.

* * * * *